(12) United States Patent
Law et al.

(10) Patent No.: US 7,214,534 B2
(45) Date of Patent: May 8, 2007

(54) ISOLATED NUCLEIC ACID MOLECULES ENCODING MUTANT μ OPIOID RECEPTORS

(75) Inventors: Ping-yee Law, Vadnais Heights, MN (US); Horace H. Loh, Little Canada, MN (US); Wanling Yang, Charleston, SC (US); Xiao-Hong Guo, St. Paul, MN (US); Patricia A. Geppert, San Antonio, TX (US)

(73) Assignee: Regents of the University of Minnesota, Minneapolis, MN (US)

( * ) Notice: Subject to any disclaimer, the term of this patent is extended or adjusted under 35 U.S.C. 154(b) by 556 days.

(21) Appl. No.: 10/465,172

(22) Filed: Jun. 18, 2003

(65) Prior Publication Data

US 2004/0096912 A1 May 20, 2004

Related U.S. Application Data

(60) Provisional application No. 60/389,862, filed on Jun. 18, 2002.

(51) Int. Cl.
| | | |
|---|---|---|
| *C12N 5/10* | (2006.01) | |
| *C12N 15/12* | (2006.01) | |
| *C12N 15/63* | (2006.01) | |
| *C12N 1/21* | (2006.01) | |
| *C12Q 1/68* | (2006.01) | |

(52) U.S. Cl. .......................... 435/325; 435/6; 435/7.1; 435/69.1; 435/252.3; 435/320.1; 530/350; 536/23.5

(58) Field of Classification Search .................... None
See application file for complete search history.

(56) References Cited

U.S. PATENT DOCUMENTS

| 5,591,602 A | 1/1997 | O'Dowd | ................... 435/69.1 |
|---|---|---|---|
| 5,804,595 A | 9/1998 | Portoghese et al. | ......... 514/428 |
| 6,235,496 B1 | 5/2001 | Yu | ............................. 435/69.1 |
| 6,270,979 B1 | 8/2001 | Sadee | ........................ 435/7.1 |

FOREIGN PATENT DOCUMENTS

| WO | WO-98/02534 | 1/1998 |
|---|---|---|
| WO | WO-00/03024 | 1/2000 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Phillips, A.J. (2001). The challenge of gene therapy and DNA delivery. J. Pharm. Pharmacology. 53:1169-1174.*
Abrahams, Mark J., et al., "Emerging therapeutic strategies for chronic pain", *Emerging Drugs*, 5 (4), Ashley Publications Ltd., (2000), 385-413.
Blomer, Ulrike, et al., "Highly efficient and sustained gene transfer in adult neurons with a lentivirus vector", *Journal of Virology*. 71(9), (Sep. 1997), 6641-6649.
Carlezon, William A., et al., "Sensitization to morphine induced by viral-mediated gene transfer", *Science*. 277(5327), (Aug. 8, 1997), 812-814.
Claude, Patricia A., "A Study of Antagonist-induced activation of Opioid Receptors with a Serine196 Mutation", *Ph.D. Thesis, University of Minnesota*, (1997).
Claude, Patricia A., et al., "Mutation of a conserved serine in TM4 of opioid receptors confers full agonistic properties to classical antagonists", *Proceedings of the National Academy of Sciences of the United States of America*. 93(12), (Jun. 1996), 5715-5719.
Kaspar, B. K., et al., "Adeno-associated virus effectively mediates conditional gene modification in the brain", *Proceedings of the National Academy of Sciences of the United States of America*, 99(4), (Feb. 19, 2002), 2320-2325.
Kong, Haeyoung, et al., "A single residue, aspartic acid 95, in the delta opioid receptor specifies selective high affinity agonist binding", *Journal of Biological Chemistry*. 268(31), (Nov. 5, 1993), 23055-23058.
Loh, Horace H., et al., "Opioid receptor knockout in mice: effects on ligand-induced analgesia and morphine lethality", *Brain Research. Molecular Brain Research*. 54(2), (Mar. 1, 1998), 321-326.
Naldini, Luigi, et al., "Efficient transfer, integration, and sustained long-term expression of the transgene in adult rat brains injected with a lentiviral vector", *Proceedings of the National Academy of Sciences of the United States of America*. 93(21), (Oct. 15, 1996), 11382-11388.
Walker, Ellen A., et al., "In vivo apparent affinity and efficacy estimates for mu opiates in a rat tail-withdrawal assay", *Psychopharmacology*. 136(1), (Mar. 1998), 15-23.
Zimmerman, D. M., et al., "Use of beta-funaltrexamine to determine mu opioid receptor involvement in the analgesic activity of various opioid ligands", *Journal of Pharmacology & Experimental Therapeutics*, 241(2), (May 1987), 374-378.
Miaskowski, Chirstine , et al., "Kappa- and delta-opioid agonists synergize to produce potent analgesia", *Brain Research*. 509(1), (Feb. 12, 1990), 165-168.

* cited by examiner

*Primary Examiner*—Christine J. Saoud
*Assistant Examiner*—Jon M Lockard
(74) *Attorney, Agent, or Firm*—Schwegman, Lundberg, Woessner & Kluth, P.A.

(57) ABSTRACT

The invention provides genetic approaches to inhibit or treat pain which employ mutant μ opioid receptors.

24 Claims, 9 Drawing Sheets

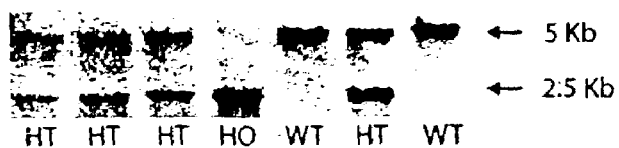
Fig.2a
Fig.2b
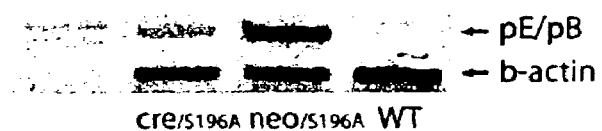
Fig.2c
Fig. 2d
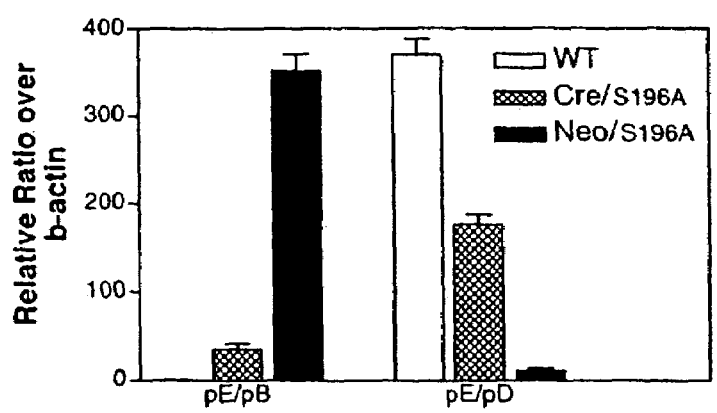
Fig. 2e
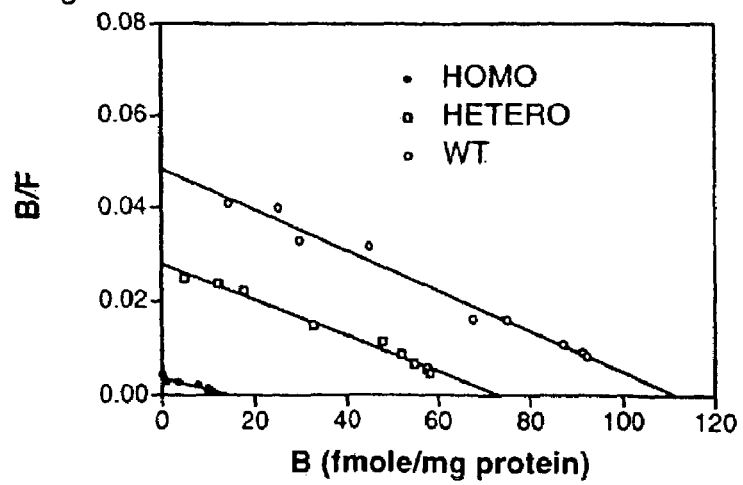

```
  1 mdssaaptna snctdalays scspapspgs wvnlshldgn lsdpcgpnrt dlggrdslcp
 61 ptgspsmita itimalysiv cvvglfgnfl vmyvivrytk mktatniyif nlaladalat
121 stlpfqsvny lmgtwpfgti lckivisidy ynmftsiftl ctmsvdryia vchpvkaldf
181 rtprnakiin vcnwilssai glpvmfmatt kyrqgsidct ltfshpfwyw enllkicvfi
241 fafimpvlii tvcyglmilr lksvrmlsgs kekdrnlrri trmvlvvvav fivcwtpihi
301 yviikalvti pettfqtvsw hfcialgytn sclnpvlyaf ldenfkrcfr efciptssni
361 eqqnstrirq ntrdhpstan tvdrtnhqle nleaetaplp
//
```

Fig 6a

```
ORIGIN
        1 mdssagpgni sdcsdplapa scspapgswl nlshvdgnqs dpcgpnrtgl ggshslcpqt
       61 gspsmvtait imalysivcv vglfgnflvm yvivrytkmk tatniyifnl aladalatst
      121 lpfqsvnylm gtwpfgnilc kivisidyyn mftsiftlct msvdryiavc hpvkaldfrt
      181 prnakivnvc nwilssaigl pvmfmattky rqgsidctlt fshptwywen llkicvfifa
      241 fimpvliitv cyglmilrlk svrmlsgske kdrnlrritr mvlvvvavfi vcwtpihiyv
      301 iikalitipe ttfqtvswhf cialgytnsc lnpvlyafld enfkrcfref ciptsstieq
      361 qnsarirqnt rehpstantv drtnhqlenl eaetaplp
//
```

Fig 6b

```
  1 mdsstgpgnt sdcsdplaqa scspapgswl nlshvdgnqs dpcglnrtgl ggndslcpqt
 61 gspsmvtait imalysivcv vglfgnflvm yvivrytkmk tatniyifnl aladalatst
121 lpfqsvnylm gtwpfgtilc kivisidyyn mftsiftlct msvdryiavc hpvkaldfrt
181 prnakivnvc nwilssaigl pvmfmattky rqgsidctlt fshptwywen llkicvfifa
241 fimpvliitv cyglmilrlk svrmlsgske kdrnlrritr mvlvvvavfi vcwtpihiyv
301 iikalitipe ttfqtvswhf cialgytnsc lnpvlyafld enfkrcfref ciptsstieq
361 qnstrvrqnt rehpstantv drtnhqlenl eaetaplp
```

Fig 6C

SEQUENCE LISTING

<160> NUMBER OF SEQ ID NOS: 9

<210> SEQ ID NO 1
<211> LENGTH: 28
<212> TYPE: DNA
<213> ORGANISM: Artificial Sequence
<220> FEATURE:
<223> OTHER INFORMATION: A synthetic primer

<400> SEQUENCE: 1
aactggatcc tctgcagcca ttggtctg                                         28

<210> SEQ ID NO 2
<211> LENGTH: 30
<212> TYPE: DNA
<213> ORGANISM: Artificial Sequence
<220> FEATURE:
<223> OTHER INFORMATION: A synthetic primer

<400> SEQUENCE: 2
cagaccaatg gctgcagaga ggatccagtt                                       30

<210> SEQ ID NO 3
<211> LENGTH: 28
<212> TYPE: DNA
<213> ORGANISM: Artificial Sequence
<220> FEATURE:
<223> OTHER INFORMATION: A synthetic primer

<400> SEQUENCE: 3
ctcaataaag acctcacaca taaagcag                                         28

<210> SEQ ID NO 4
<211> LENGTH: 34

-continued

```
<212> TYPE: DNA
<213> ORGANISM: Artificial Sequence
<220> FEATURE:
<223> OTHER INFORMATION: A synthetic primer

<400> SEQUENCE: 4
gtatagcata cattatacga agttgttgaa gccg                                34

<210> SEQ ID NO 5
<211> LENGTH: 22
<212> TYPE: DNA
<213> ORGANISM: Mus musculus

<400> SEQUENCE: 5
ctacattttc aaccttgctc tg                                             22

<210> SEQ ID NO 6
<211> LENGTH: 20
<212> TYPE: DNA
<213> ORGANISM: Mus musculus

<400> SEQUENCE: 6
gagcaggttc tcccagtacc                                                20

<210> SEQ ID NO 7
<211> LENGTH: 400
<212> TYPE: PRT
<213> ORGANISM: Homo sapiens

<400> SEQUENCE: 7
```

Met Asp Ser Ser Ala Ala Pro Thr Asn Ala Ser Asn Cys Thr Asp Ala
 1               5                  10                  15

Leu Ala Tyr Ser Ser Cys Ser Pro Ala Pro Ser Pro Gly Ser Trp Val
             20                  25                  30

Asn Leu Ser His Leu Asp Gly Asn Leu Ser Asp Pro Cys Gly Pro Asp
         35                  40                  45

Arg Thr Asn Leu Gly Gly Arg Asp Ser Leu Cys Pro Pro Thr Gly Ser
     50                  55                  60

Pro Ser Met Ile Thr Ala Ile Thr Ile Met Ala Leu Tyr Ser Ile Val
 65                  70                  75                  80

Cys Val Val Gly Leu Phe Gly Asn Phe Leu Val Met Tyr Val Ile Val
                 85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

-continued

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
            245                 250                 255

Met Ile Leu Arg Leu Lys Ser Val Arg Met Leu Ser Gly Ser Lys Glu
        260                 265                 270

Lys Asp Arg Asn Leu Arg Arg Ile Thr Arg Met Val Leu Val Val Val
    275                 280                 285

Ala Val Phe Ile Val Cys Trp Thr Pro Ile His Ile Tyr Val Ile Ile
    290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
            325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
        355                 360                 365

Arg Gln Asn Thr Arg Asp His Pro Ser Thr Ala Asn Thr Val Asp Arg
    370                 375                 380

Thr Asn His Gln Leu Glu Asn Leu Glu Ala Glu Thr Ala Pro Leu Pro
385                 390                 395                 400

<210> SEQ ID NO 8
<211> LENGTH: 398
<212> TYPE: PRT
<213> ORGANISM: Mus musculus

<400> SEQUENCE: 8

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65              70                  75                  80

Val Gly Leu Phe Gly Asn Phe Leu Val Met Tyr Val Ile Val Arg Tyr
            85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

```
Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Ala Arg Ile Arg Gln
        355                 360                 365

Asn Thr Arg Glu His Pro Ser Thr Ala Asn Thr Val Asp Arg Thr Asn
    370                 375                 380

His Gln Leu Glu Asn Leu Glu Ala Glu Thr Ala Pro Leu Pro
385                 390                 395

<210> SEQ ID NO 9
<211> LENGTH: 398
<212> TYPE: PRT
<213> ORGANISM: Rattus norvegicus

<400> SEQUENCE: 9

Met Asp Ser Ser Thr Gly Pro Gly Asn Thr Ser Asp Cys Ser Asp Pro
1               5                   10                  15

Leu Ala Gln Ala Ser Cys Ser Pro Ala Pro Gly Ser Trp Leu Asn Leu
            20                  25                  30

Ser His Val Asp Gly Asn Gln Ser Asp Pro Cys Gly Leu Asn Arg Thr
        35                  40                  45

Gly Leu Gly Gly Asn Asp Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Thr Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
```

```
                    180                 185                 190
Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
        210                 215                 220

Thr Trp Tyr Trp Glu Asn Leu Leu Lys Ile Cys Val Phe Ile Phe Ala
225                 230                 235                 240

Phe Ile Met Pro Ile Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285

Phe Ile Val Cys Trp Thr Pro Ile His Ile Tyr Val Ile Ile Lys Ala
        290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Thr Arg Val Arg Gln
        355                 360                 365

Asn Thr Arg Glu His Pro Ser Thr Ala Asn Thr Val Asp Arg Thr Asn
        370                 375                 380

His Gln Leu Glu Asn Leu Glu Ala Glu Thr Ala Pro Leu Pro
385                 390                 395
```

ISOLATED NUCLEIC ACID MOLECULES ENCODING MUTANT μ OPIOID RECEPTORS

CROSS-REFERENCE TO RELATED APPLICATIONS

This application claims the benefit of the filing date of U.S. application Ser. No. 60/389,862, filed on Jun. 18, 2002, the disclosure of which is incorporated by reference herein.

STATEMENT OF GOVERNMENT RIGHTS

The invention was made, at least in part, with grants from the Government of the United States of America (grants DA00564, DA01583, and DA07339 from the National Institute on Drug Abuse). The Government may have certain rights to the invention.

BACKGROUND OF THE INVENTION

Among the agents used in pain management, opioid analgesics are the most efficacious in controlling moderate and severe post-operative pain. However, opioid analgesics have well-known adverse effects such as respiratory depression, constipation, nausea, and neurotoxicity (Bruera et al., 1999), as well as tolerance and physical dependence. Decades of research have focused on designing an opioid analgesic that has the analgesic efficacy of morphine but is devoid of its adverse effects.

Pharmacological studies have defined three classes of opioid receptors, the δ, κ, and μ opioid receptors. One approach to develop agents having opioid analgesic efficacy in the absence of tolerance and/or physical dependence is to develop opioid drugs that selectively target one or a subset of opioid receptors. Another approach is the use of recombinant, e.g., mutant, opioid receptors. For example, Carlezon et al. (1997) overexpressed the AMPA receptor subunit GluR1 in the ventral tegmental area (VTA) using herpes simplex virus-mediated gene transfer. Carlezon et al. found that the expression of GluR1 increased the sensitization of virally-transduced animals to morphine's stimulant and rewarding effects. Kong et al. (1993) substituted aspartic acid 95 in transmembrane segment 2 of the cloned mouse δ opioid receptor with an asparagine (D95N). The D95N mutant receptor had reduced affinity for δ receptor-selective agonists such as enkephalin, [D-Pen$^2$, D-Pen$^5$]enkephalin and [D-Ser$^2$,Leu$^5$]enkephalin-Thr6. The binding of δ-selective non-peptide agonists was also reduced. In contrast, δ receptor-selective antagonists, such as naltrindole, the benzofuran analog of naltrindole, and 7-benyllidenenaltrexone, bound equally well to the wild-type and mutant receptor. Non-selective opioid agonists such as bremazocine and buprenorphine, which interact with δ, κ, and μ opioid receptors, showed no difference in binding to the wild-type and mutant δ receptor.

Claude et al. (1996) investigated the involvement of a conserved serine (Ser$^{196}$ at the μ, Ser$^{177}$ at the δ, and Ser$^{187}$ at the κ opioid receptor) in receptor activation. Claude et al. noted that classical opioid antagonists such as naloxone, naltrexone, naltriben, and H-Try-Tic[ψCH$_2$NH]Phe-Phe-OH (TIPPψ, Tic=1,2,3,4-tetrahydroisoquinoline-3-carboxylic acid) could inhibit forskolin-stimulated adenylyl cyclase activity in CHO cells stably expressing a μ/δ opioid chimeric receptor, μδ$_2$. Antagonists also activated the G protein-coupled inward rectifying potassium channel (GIRK1) in Xenopus oocytes coexpressing the μδ2 opioid receptor and the GIRK1 channel. In vitro experiments in which the Ser$^{196}$ residue of the μ opioid receptor was substituted with other amino acids, indicated that a mutation of Ser$^{196}$ to Ala resulted in greater agonistic efficacy with classical opioid antagonists (Claude, 1997).

What is needed is an improved method to identify agents that have desirable effects of opioids in the absence of unwanted side effects.

SUMMARY OF THE INVENTION

The invention provides a genetic approach to inhibit or treat pain, e.g., chronic or surgical pain, in a mammal which employs mutant μ opioid receptors. The method comprises contacting a mammal with a composition comprising a recombinant nucleic acid molecule (polynucleotide) comprising a promoter operably linked to a nucleic acid sequence encoding a mutant μ opioid receptor, or a portion thereof with substantially the same activity as the corresponding full-length mutant μ opioid receptor, and an antagonist of a corresponding wild-type μ opioid receptor in an amount effective to inhibit or treat pain in the mammal. Preferably, the mammal is a human, however, the invention may be practiced with non-human mammals including, but not limited to, a non-human primate, rodent, ovine, bovine, equine, swine, canine, feline or caprine. In one embodiment of the invention, the composition is administered to neurons, e.g., nociceptive neurons, at or near a site in the mammal associated with pain or at risk of being associated with pain. However, the composition may be administered via other routes. Preferably, the composition comprises a recombinant virus comprising the recombinant nucleic acid molecule, e.g., a recombinant retrovirus, lentivirus, adenovirus, herpes virus or adeno-associated virus. Preferred viruses include those which can infect neurons, e.g., nociceptive neurons.

As described hereinbelow, a population of homozygous mice having a knock-in of the S196A mutation into the MOR-1 gene (murine μ opioid receptor) was prepared. The opioid antagonists naloxone and nalorphine exhibited agonistic properties similar to those of morphine in the mutant mice. These studies indicated that opioid antagonists can be employed to activate a mutant μ opioid receptor. However, in both in vitro and in vivo data, the antagonists did not exhibit full efficacy as an agonist. As further described hereinbelow, substitutions in at least two positions, for instance, substitutions in transmembrane region (TM) 1, 4 or 7 of the μ opioid receptor, can result in a mutant μ opioid receptor with desirable properties. Thus, substitutions in a μ opioid receptor corresponding to human TM4 (residues 188 to 209), murine TM4 (residues 186 to 207), human TM7 (residues 320 to 341) and/or murine TM7 (residues 318 to 339) are useful to prepare mutant μ opioid receptors with desirable properties. For example, a mutation in TM4, e.g., murine S196A or S196L, and a mutation in TM7, e.g., murine T327A or C330S, results in a mutant μ opioid receptor that, when contacted with a classical antagonist, such as naloxone or naltrexone, elicits a signal corresponding to one elicited by a full agonist. Such mutant receptors are useful in the treatment of chronic pain.

The invention thus provides an isolated nucleic acid and molecule comprising a nucleic acid sequence encoding a mutant μ opioid receptor, e.g., a mutant receptor having two or more substitutions in one or more transmembrane regions, which substitutions result in a mutant μ opioid receptor which is activated by an antagonist of the wild-type μ opioid receptor. Preferred transmembrane regions for the substitutions are TM1, TM4 or TM7 or TM4 and TM7.

Preferred substitutions are at positions corresponding to position 196 in murine TM4, position 327 in murine TM7 or position 330 in murine TM7. Preferred substitutions are conservative substitutions, e.g., substitutions of serine, leucine, alanine, phenylalanine, isoleucine, valine, glycine, threonine or cysteine for each other. In one embodiment, preferred substitutions are substitutions of serine, leucine, alanine, isoleucine, valine, glycine, threonine or cysteine for each other. In one embodiment, the nucleic acid molecule of the invention encodes a polypeptide having substantial identity to SEQ ID NO:7, SEQ ID NO:8, or SEQ ID NO:9. Preferably, the expression of the nucleic acid sequence encoding the mutant μ opioid receptor, e.g., a receptor comprising a mutation in TM4 corresponding to murine S196A or S196L, and a mutation in TM7 corresponding to murine T327A or C330S, is controlled by a tissueor cell-specific promoter and/or enhancer. In one embodiment, the 5' transcription regulatory element is the promoter and enhancer of the μ opioid receptor gene. Moreover, the invention envisions nucleic acid molecules encoding mutant μ opioid receptors with other substitutions, including substitutions in receptor phosphorylation sites. The invention also provides expression cassettes, vectors and cells comprising the nucleic acid molecule of the invention, and isolated mutant μ opioid receptor polypeptide.

In particular, the delivery of a recombinant nucleic acid molecule encoding a mutant μ opioid receptor, optionally in a biological delivery vehicle, into neurons in critical pain pathways is envisioned. For example, delivery systems such as viral delivery, including adenovirus or lentivirus vectors, can be used to specifically deliver and express mutant μ opioid receptors associated with phenotypes that are desirable relative to the endogenous (wild-type) receptors (see, e.g., Kaspar et al., 2002; Bloomer et al., 1997; Naldini et al., 1996). Activation of these mutant receptors via administration of an antagonist of the wild-type μ opioid receptor, e.g., naloxone or naltrexone, at the proper segment of the spinal cord, such as at the nociceptive neurons, activates the mutant μ opioid receptor but not the endogenous receptors. Pain transmission through the segment of spinal cord that expresses the mutant receptor is then blocked. Thus, localized expression of the mutant receptor in conjunction with opioid administration produces the analgesic effect of the administered drug without causing the adverse effects related to the activation of the endogenous opioid receptors.

The invention also provides a method of using a mutant μ opioid receptor polypeptide, e.g., in a method to identify an agent that is an agonist of a mutant μ opioid receptor and an antagonist of the wild-type μ opioid receptor. Further provided is a method to detect a mutant μ opioid receptor which is activated upon contact with an antagonist of a corresponding wild-type μ opioid receptor.

BRIEF DESCRIPTION OF THE FIGURES

FIG. 2. Characterization of the expression of μ opioid receptor S196A. A) Screening of mutant mice by Southern blotting using 5' probe. Mouse genomic DNA was digested with PstI and hybridized to $^{32}$P labeled 5' probe (see FIG. 1B). The 2.5 kb band represents the mutant allele and the 5 kb band represent the wild-type allele. WT: wild-type; HO: Cre/S196A homozygous mutant mice; HT: Cre/S196A heterozygous mice. B) RT-PCR analysis of correctly spliced MOR-1 mRNA using primers pE and pD (shown in FIG. 1). C) RT-PCR analysis of incorrectly spliced MOR-1 mRNA (intron 2 inclusion) using primers pE and pB (shown in FIG. 1). D) Quantitation of MOR-1 mRNA normalized by β-actin signal. The y-axis is the relative ratio of MOR-1 over β-actin signal. Cre/S196A: homozygous Cre/S196A mice, Neo/S196A: homozygous mutant mice with neo in intron 2. E) Scatchard analysis of [$^3$H]DAMGO saturation binding of brain membranes from homozygous Cre/S196A (HOMO) mutant mice, heterozygous Cre/S196A mice (HETERO) and wild-type littermates (WT). The $K_d$ and $B_{max}$ respectively are: homozygous: 6.33 nM, 17.5 fmol/mg protein; heterozygous mice: 2.45 nM, 72.15 fmole/mg protein; wild-type mice: 2.59 nM and 112.6 mg protein.

0.24–0.74 mg/kg) for wild-type littermates. *: P<0.05; **: P<0.01 as compared between genotypes in the same dose group, n=10–12.

FIG. 6. Amino acid sequence of wild-type human (A) (SEQ ID NO:7), murine (B) (SEQ ID NO:8) and rat (C) (SEQ ID NO:9) μ opioid receptor.

Figure 7:
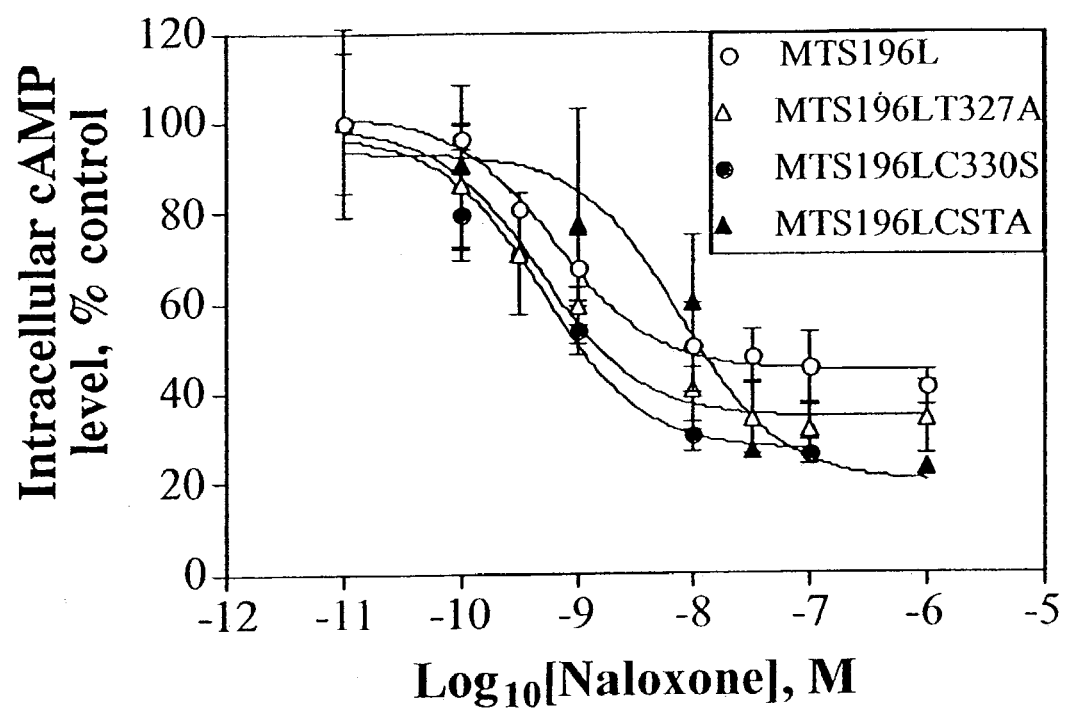

FIG. 7. Mutation of amino acids in TM7 of the S196L μ opioid receptor mutant increases the maximal activity of the antagonist naloxone. The ability of various concentrations of naloxone to inhibit the 10 μM for skolin-stimulated production of intracellular cAMP level in HEK293 cells expressing various μ opioid receptor mutants was tested. The amount of cAMP produced in the presence of naloxone was compared to the control level and the values from a minimum of 4 dose-response studies averaged and fitted by the Graphpad Prism program. S196LCSTA represents the combination of the S196L, T327A and C330S mutations in the same receptor mutant.

DETAILED DESCRIPTION OF THE INVENTION

I. Definitions

As used herein, an "agonist" is a molecule which binds to a particular physiological receptor and mimics the effect of one or more endogenous regulatory compounds. A "partial agonist" is a molecule that is only partly effective as an agonist. An "antagonist" is a molecule that binds to a particular receptor and does not mimic but rather interferes with the binding of a naturally occuring agonist to the receptor. Thus, an antagonist is devoid of intrinsic regulatory activity but produces a detectable effect by inhibiting the action of an agonist.

As used herein, the terms "isolated and/or purified" refer to in vitro preparation, isolation and/or purification of a nucleic acid molecule or polypeptide of the invention, so that it is not associated with in vivo substances. Thus, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. An isolated nucleic acid molecule means a polymeric form of nucleotides of at least 10 bases in length, either ribonucleotides or deoxynucleotides or a modified form of either type of nucleotide. The term includes single and double stranded forms of DNA.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al. (1981) and Goeddel et al. (1980). Therefore, "preselected DNA" includes completely synthetic DNA sequences, semi-synthetic DNA sequences, DNA sequences isolated from biological sources, and DNA sequences derived from RNA, as well as mixtures thereof.

The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably, oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a nucleotide substitution variant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phophoroselenoate, phosphorodiselenoate, phosphoroanilothioate, phosphoraniladate, phosphoroamidate, and the like. An oligonucleotide can include a label for detection, if desired.

The term "isolated polypeptide" means a polypeptide encoded by cDNA or recombinant RNA, or is synthetic origin, or some combination thereof, which isolated polypeptide (1) is not associated with proteins found in nature, (2) is free of other proteins from the same source, e.g., free of human proteins, (3) is expressed by a cell from a different species, or (4) does not occur in nature.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of sequence from a mutant μ opioid receptor that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff (1972), and the supplement thereto. The two sequences or parts thereof are more preferably homologous if their amino acids are greater than or equal to 50% identical when optimally aligned using the ALIGN program.

The term "corresponds to" is used herein to mean that a polynucleotide or polypeptide sequence is homologous to all or a portion of a reference polynucleotide or polypeptide sequence. In contradistinction, the term "complementary to" is used herein to mean that the complementary polynucleotide sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20–50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two polypeptide sequences, when optimally aligned, such as by the programs GAP or BESTFIT using default gap weights, share at least about 80 percent sequence identity, preferably at least about 90 percent sequence identity, more preferably at least about 95 percent sequence identity, and most preferably at least about 99 percent sequence identity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

As used herein, "chimeric" means that a vector comprises DNA from at least two different species, or comprises DNA from the same species, which is linked or associated in a manner which does not occur in the "native" or wild type of the species.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

A "promoter" is a region of a DNA molecule typically within about 100 nucleotide pairs 5' of the point at which transcription begins (i.e., a transcription start site). That region typically contains several types of DNA sequence elements that are located in similar relative positions in different genes.

Another type of discrete transcription regulatory sequence element is an "enhancer." An enhancer may provide specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well-known in the art. As is also well-known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking may accomplished ligation at convenient restriction sites. If such sites do not exist, synthetic oligonucleotide adaptors or linkers are used in accord with conventional practice.

As used herein, the term "cell line" is intended to refer to well-characterized homogenous, biologically pure populations of cells. These cells may be eukaryotic cells that are neoplastic or which have been "immortalized" in vitro by methods known in the art, or prokaryotic cells. A "host cell" may be any eukaryotic or prokaryotic cell, including primary cells. The cell line or host cell is preferably of mammalian origin, but cell lines or host cells of non-mammalian origin may be employed, including plant, insect, yeast, fungal or bacterial sources.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The cells of the present invention are typically produced by transfection with an isolated linear DNA sequence, a DNA sequence in a plasmid or other expression vector, e.g., a viral expression vector, or by infection with a recombinant virus.

As used herein, the term "derived" with respect to a RNA molecule means that the RNA molecule has complementary sequence identity to a particular DNA molecule.

II. Polynucleotides and Polypeptides of the Invention

A. Isolated Polynucleotides That Encode a Mutant µ Opioid Receptor

1. Sources of Nucleic Acid Molecules Encoding µ Opioid Receptors

Sources of nucleotide sequences from which the present nucleic acid molecules encoding a mutant µ opioid receptor or the nucleic acid complement thereof may be prepared, include total or polyA$^+$ RNA from any eukaryotic, preferably mammalian, cellular source from which cDNAs can be derived by methods known in the art. Other sources of the DNA molecules of the invention include genomic libraries derived from any eukaryotic cellular source. Preferred sources include human, non-human primate, rodent, ovine, bovine, equine, swine, canine, feline or caprine cells.

2. Isolation of a Gene Encoding a µ Opioid Receptor

A nucleic acid molecule encoding a µ opioid receptor can be identified and isolated using standard methods, as described by Sambrook et al. (2001). For example, reverse-transcriptase PCR (RT-PCR) can be employed to isolate and clone µ opioid receptor cDNAs. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (GIBCO-BRL™/Life Technologies, Gaithersburg, Md). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al (1987); and Erlich (1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of other eukaryotic µ opioid receptors. One primer is prepared which is predicted to anneal to the antisense strand, and another primer prepared which is predicted to anneal to the sense strand, of a DNA molecule which encodes a µ opioid receptor.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone cDNAs which encode a µ opioid receptor is to screen a cDNA library. Screening for DNA fragments that encode all or a portion of a cDNA encoding a µ opioid receptor can be accomplished by probing the library with a probe which has sequences that are highly conserved between genes believed to be related to the μ opioid receptor, e.g., the homolog of a particular μ opioid receptor from a different species, or by screening of plaques for binding to antibodies that specifically recognize the μ opioid receptor. DNA fragments that bind to a probe having sequences which are related to the μ opioid receptor, or which are immunoreactive with antibodies to the μ opioid receptor, can be subcloned into a suitable vector and sequenced and/or used as probes to identify other cDNAs encoding all or a portion of the μ opioid receptor.

3. Preparation of the Nucleic Acid Molecules of the Invention

Nucleic acid molecules encoding amino acid sequence variants of a μ opioid receptor are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the μ opioid receptor.

Oligonucleotide-mediated mutagenesis is a preferred method for preparing amino acid substitution variants of a mutant μ opioid receptor. This technique is well known in the art as described by Adelman et al. (1983). Briefly, μ opioid receptor DNA is altered by hybridizing an oligonucleotide encoding the desired mutation to a DNA template, where the template is the single-stranded form of a plasmid or bacteriophage containing the unaltered or native DNA sequence of the μ opioid receptor. After hybridization, a DNA polymerase is used to synthesize an entire second complementary strand of the template that will thus incorporate the oligonucleotide primer, and will code for the selected alteration in the μ opioid receptor DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al. (1987). Thus, the DNA that is to be mutated may be inserted into one of these vectors to generate single-stranded template. Production of the single-stranded template is described in Sambrook et al. (2001).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the μ opioid receptor, and the other strand (the original template) encodes the native, unaltered sequence of the μ opioid receptor. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(αS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(αS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

Thus, the present invention provides an isolated polynucleotide that encodes a mutant μ opioid receptor polypeptide or a portion thereof with substantially the same activity as the corresponding full-length mutant μ opioid receptor. In one embodiment, the polynucleotide of the invention encodes a mutant μ opioid receptor that comprises two or more amino acid substitutions which result in a receptor that is activated when it is contacted with an antagonist of the wild-type receptor, i.e., the antagonist of the wild-type receptor is an agonist when bound to the mutant receptor. The substitutions are preferably in transmembrane regions (TM) of the μ opioid receptor, and preferably in TM1, TM4, TM7, or any combination thereof.

B. Polypeptides of the Invention

The present isolated or purified mutant μ opioid receptor, a portion thereof with substantially the same activity as the corresponding full-length mutant μ opioid receptor, or a derivative thereof, can be synthesized in vitro, e.g., by the solid phase peptide synthetic method or by recombinant DNA approaches (see above). The solid phase peptide synthetic method is an established and widely used method, which is described in the following references: Stewart et al. (1969); Merrifield (1963); Meienhofer (1973); Bavaay and Merrifield (1980); and Clark-Lewis et al. (1997). These peptides can be further purified by fractionation on immunoaffinity or ion-exchange columns; ethanol precipitation; reverse phase HPLC; chromatography on silica or on an anion-exchange resin such as DEAE; chromatofocusing;

SDS-PAGE; ammonium sulfate precipitation; gel filtration using, for example, Sephadex G-75; or ligand affinity chromatography.

Once isolated and characterized, derivatives, e.g., chemically derived derivatives, of a given mutant μ opioid receptor can be readily prepared. For example, amides of the mutant μ opioid receptor of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of a polypeptide of the invention may be prepared in the usual manner by contacting the polypeptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the mutant μ opioid receptors may be prepared by utilizing an N-acyl protected amino acid for the final condensation, or by acylating a protected or unprotected polypeptide. O-acyl derivatives may be prepared, for example, by acylation of a free hydroxy polypeptide or polypeptide resin. Either acylation may be carried out using standard acylating reagents such as acyl halides, anhydrides, acyl imidazoles, and the like. Both - and O-acylation may be carried out together, if desired.

Formyl-methionine, pyroglutamine and trimethyl-alanine may be substituted at the N-terminal residue of the polypeptide. Other amino-terminal modifications include aminooxy-pentane modifications (see Simmons et al. (1997).

The mutant μ opioid receptors of the invention include the substitution of at least one and preferably at least two amino acid residues in the polypeptide. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic; trp, tyr, phe.

Substitution of like amino acids can also be made on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In such changes, the substitution of amino acids whose hydrophilicity values are within ±2 is preferred, those which are within ±1 are particularly preferred, and those within ±0.5 are even more particularly preferred.

Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferably, the substitutions are in one or more transmembrane regions of the receptor and are conservative substitutions, e.g., substitutions of serine, leucine, alanine, isoleucine, valine, glycine, threonine or cysteine for each other.

Exemplary substitutions include those in Table 1.

TABLE 1

| Original Residue | Exemplary Substitutions |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr; Ala; Leu |
| Thr | Ser; Ala |
| Trp | Tyr |
| Tyr | Trp; Phe |
| Val | Ile; Leu |

After the substitutions are introduced, the resulting mutant receptor is screened for activity.

Acid addition salts of the polypeptide or of amino residues of the polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

Accordingly, the present invention contemplates an isolated mutant μ opioid receptor polypeptide. Preferably, a mutant μ opioid receptor polypeptide of the invention is a recombinant polypeptide. A mutant μ opioid receptor polypeptide preferably comprises less than about 500 amino acid residues and, more preferably less than about 400 amino acid residues.

Amino acid residues can be added to or deleted from a full-length mutant μ opioid receptor polypeptide through the use of standard molecular biological techniques without altering the functionality of the receptor. For example, portions of the mutant μ opioid receptor can be removed to create truncated mutant μ opioid receptors. The truncated receptor retains the properties of the full-length mutant μ opioid receptors, e.g., the binding of an antagonist of a wild-type receptor to the mutant receptor activates the mutant receptor. As used herein, truncated receptors are receptors in which amino acids have been removed from the mutant receptor to create a shorter mutant receptor. As used herein, chimeric receptors are receptors in which amino acids have been added to a mutant receptor or a truncated mutant receptor, i.e., non-μ opioid receptor residues, which chimeric receptor retains the properties of the full-length mutant μ receptor.

C. Expression Cassettes, Vectors and Cells of the Invention

1. Chimeric Expression Cassettes

To prepare expression cassettes for transformation, the recombinant DNA sequence or segment may be circular or linear, double-stranded or single-stranded. A recombinant DNA sequence which encodes a RNA sequence that is substantially complementary to a mRNA sequence encoding a mutant μ opioid receptor is typically a "sense" DNA sequence cloned into a cassette in the opposite orientation (i.e., 3' to 5' rather than 5' to 3'). Generally, the recombinant DNA sequence or segment is in the form of chimeric DNA, such as plasmid DNA, that can also contain coding regions flanked by control sequences which promote the expression of the recombinant DNA present in the resultant cell.

Aside from recombinant DNA sequences that serve as transcription units for a mutant μ opioid receptor, or portions thereof, a portion of the recombinant DNA may be untranscribed, serving a regulatory or a structural function. For example, the recombinant DNA may itself comprise a promoter that is active in mammalian cells, or may utilize a promoter already present in the genome that is the transformation target. Such promoters include the CMV promoter, as well as the SV40 late promoter, adenoviral promoter and lentiviral and retroviral LTRs (long terminal repeat elements), although many other promoter elements well known to the art may be employed in the practice of the invention.

Other elements functional in the cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

A coding sequence of an expression cassette may also be operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed RNA. Transcription-terminating regions are well-known in the art.

The recombinant DNA to be introduced into the cells may contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of E. coli, the beta-glucuronidase gene (gus) of the uidA locus of E. coli, and the luciferase gene from firefly Photinus pyralis. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, Sambrook et al. (2001) provides suitable methods of construction.

The present invention thus provides an expression cassette or vector comprising a polynucleotide of the invention, i.e., one that encodes a mutant μ opioid receptor polypeptide or a portion thereof with substantially the same activity as the full-length mutant μ opioid receptor polypeptide. More preferably, expression cassettes and vectors of the present invention comprise a promoter, or optionally a promoter, or optionally an enhancer-promoter, operably linked to the polynucleotide. An enhancer-promoter used in an expression cassette of the present invention can be any enhancer-promoter that drives expression in a cell to be transfected. By employing an enhancer-promoter with well-known properties, the level and pattern of gene product expression can be optimized. More preferably still, expression cassette of the invention comprise a polynucleotide operatively linked to a tissue- or cell-specific promoter. Exemplary vectors for the expression cassette include viral vectors, e.g., adenovirus or lentivirus vectors.

An expression cassette of the present invention is useful both as a means for preparing quantities of the mutant μ opioid receptor polypeptide encoding DNA itself, and as a means for preparing the encoded polypeptides. It is contemplated that where mutant μ opioid receptor polypeptides of the invention are made by recombinant means, one can employ either prokaryotic or eukaryotic expression vectors as shuttle systems.

2. Introduction into Cells

The recombinant DNA can be readily introduced into the cells, e.g., mammalian, bacterial, yeast or insect cells, by transfection with an expression cassette or vector comprising DNA encoding a mutant μ opioid receptor or its complement, by any procedure useful for the introduction into a particular cell, e.g., physical or biological methods, to yield a transformed cell having the recombinant DNA optionally stably integrated into its genome, so that the DNA molecules, sequences, or segments, of the present invention are expressed by the cell.

Physical methods to introduce a recombinant DNA into a cell include calcium, DEAE-dextran, lipofection, particle bombardment, protoplast fusion, microinjection, electroporation, and the like. A widely used method is transfection mediated by either calcium phosphate or DEAE-dextran. Depending on the cell type, up to 90% of a population of cultured cells can be transfected at any one time. Because of its high efficiency, transfection mediated by calcium phosphate or DEAE-dextran may be the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

Biological methods to introduce the DNA of interest into a cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. For mammalian cells, it may be desirable to use an efficient means of precisely inserting a single copy gene into the host genome. Viral vectors, and especially retroviral and lentiviral vectors, have become widely used method for inserting genes into mammalian, e.g., human cells. Other viral vectors can be derived from poxviruses, herpes simplex virus I, adenoviruses and adeno-associated viruses, and the like.

A transfected or infected cell can be prokaryotic or eukaryotic. Preferably, the transfected or infected cell of the invention is a eukaryotic cell, more preferably a vertebrate cell, and even more preferably a mammalian cell.

Examples of useful cell lines include but are not limited to AtT-20, VERO and HeLa cells, Chinese hamster ovary (CHO) cell lines, and W138, BHK, COSM6, COS-1, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, adenovirus 2, cytomegalovirus, simian virus 40 (SV40), e.g., the early and late promoters of SV40 virus, and lentivirus or retrovirus LTRS. Further, it is also possible, and often desirable, to utilize promoter or control sequences normally associated with the desired gene sequence, provided such control sequences are compatible with the host cell systems.

An origin of replication can be provided with by construction of the vector to include an exogenous origin, such as can be derived from SV40 or other viral (e.g., Polyoma, Adeno, VSV, BPV, CMV) source, or can be provided by the cell chromosomal replication mechanism.

In another aspect, the recombinant cells of the present invention are prokaryotic cells. Preferably, the recombinant cells of the invention are bacterial cells of the DH5a strain of *Escherichia coli*, as well as *E. coli* W3110 (F, λ, prototrophic, ATCC No. 273325), bacilli such as *Bacillus subtilis*, or other enterobacteriaceae such as *Salmonella typhimurium* or *Serratia marcesceus*, and various *Pseudomonas* species. In general, prokaryotes are preferred for the initial cloning of DNA sequences and constructing the vectors useful in the invention. For example, *E. coli* K12 strains can be particularly useful. Other microbial strains which can be used include *E. coli* B, and *E. coli* X1776 (ATCC No. 31537). These examples are, of course, intended to be illustrative rather than limiting.

In general, plasmid vectors containing replicon and control sequences which are derived from species compatible with the cell are used in connection with these cells. The vector ordinarily carries a replication site, as well as marking sequences which are capable of providing phenotypic selection in transformed cells. For example, *E. coli* can be transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (Chang et al., 1978; Itakura et al., 1977; Goeddel et al., 1979; Goeddel et al., 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to introduce functional promoters into plasmid vectors (Siebwenlist et al., 1980).

In addition to prokaryotes, eukaryotic microbes, such as yeast can also be used. *Saccharomyces cerevisiae* or common baker's yeast is the most commonly used among eukaryotic microorganisms, although *Schizosaccharomyces* and *Pichia* are commonly available. For expression in *Saccharomyces*, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076. The presence of the trpl lesion as a characteristic of the yeast cell genome then provides an effective environment for detecting transformation by growth in the absence of tryptophan.

Suitable promoter sequences in yeast vectors include the promoters for 3-phosphoglycerate kinase (Hitzeman et al., 1980) or other glycolytic enzymes (Hess et al., 1968; Holland et al., 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utlization Any plasmid vector containing a yeast-compatible promoter, origin or replication and termination sequences is suitable.

To confirm the presence of the recombinant DNA sequence in the cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular mutant μ opioid receptor, e.g., by immunological means (ELISAs and Western blots) or by assays described herein.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the cell.

A recombinant mutant μ opioid receptor polypeptide may be recovered or collected either from the transfected or infected cells or the medium in which those cells are cultured. Recovery comprises isolating and purifying the recombinant polypeptide. Isolation and purification techniques for polypeptides are well-known in the art and include such procedures as precipitation, filtration, chromatography, electrophoresis and the like.

III. Pharmaceutical Compositions

Administration of a nucleic acid molecule of the invention may be accomplished through the introduction of cells transformed with an expression cassette comprising the nucleic acid molecule (see, for example, WO 93/02556), the administration of a recombinant virus, or the administration of the nucleic acid molecule (see, for example, Felgner et al., U.S. Pat. No. 5,580,859, Pardoll et al. (1995); Stevenson et al. (1995); Molling (1997); Donnelly et al. (1995); Yang et al. (1996); Abdallah et al. (1995)). In a preferred embodiment, the present invention provides pharmaceutical compositions comprising a nucleic acid molecule encoding a mutant μ opioid receptor and a physiologically acceptable carrier. More preferably, a pharmaceutical composition comprises a recombinant virus comprising a nucleic acid molecule encoding a mutant μ opioid receptor polypeptide and a physiologically acceptable carrier. By "physiologically acceptable" or "pharmaceutically acceptable" it is meant the carrier, diluent, excipient, and/or salt must be compatible with the other ingredients of the formulation, and not deleterious to the recipient thereof.

A composition of the present invention is typically administered parenterally in dosage unit formulations containing standard, well-known nontoxic physiologically acceptable carriers, adjuvants, and vehicles as desired. The term parenteral as used herein includes intrathecal, intravenous, intramuscular, iniraarterial injection, or infusion techniques.

Administration of a composition of the invention in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated.

One or more suitable unit dosage forms comprising a composition of the invention of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathecal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the composition with liquid carriers, solid matrices, semi-solid carriers, finely divided solid carriers or combinations thereof, and then, if necessary, introducing or shaping the product into the desired delivery system.

Pharmaceutical formulations containing the composition of the invention can be prepared by procedures known in the art using well known and readily available ingredients. For example, the composition can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the compositions of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of the invention are designed to resist disintegration in the stomach and dissolve in the more neutral to alkaline environment of the duodenum.

The compositions of the invention can also be formulated as elixirs or solutions for convenient oral administration or as solutions appropriate for parenteral administration, for instance by intramuscular, subcutaneous or intravenous routes and preferably by intrathecal routes.

The pharmaceutical formulations of the invention can also take the form of an aqueous or anhydrous solution or dispersion, or alternatively the form of an emulsion or suspension.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well-known in the art (see, e.g. Gabizon, et al., 1990; Ferruti, et al., 1986; and Ranade, 1989).

A transfected or an infected cell, e.g., one infected with helper-free virus, can also serve as a carrier. By way of example, a neuronal cell can be removed from an organism, transfected with a polynucleotide of the present invention using methods set forth above and then the transfected cell returned to the organism (e.g., injected intrathecally).

Thus, the composition may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the composition may be well suited to formulation as sustained release dosage forms and the like. The coatings, envelopes, and protective matrices may be made, for example, from polymeric substances, such as polylactide-glycolates, liposomes, microemulsions, microparticles, nanoparticles, or waxes.

The compositions of the invention can be delivered via patches for transdermal administration. See U.S. Pat. No. 5,560,922 for examples of patches suitable for transdermal delivery of a therapeutic agent. Agents released from a transdermal delivery system must be capable of penetrating each layer of skin. In order to increase the rate of permeation of the agent, a transdermal delivery system must be able in particular to increase the permeability of the outermost layer of skin, the stratum corneum, which provides the most resistance to the penetration of molecules. The fabrication of patches for transdermal delivery of agents is well known to the art.

For administration to the upper (nasal) or lower respiratory tract by inhalation, the compositions of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the composition and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the composition may be administered via nose drops, a liquid spray, such as via a plastic bottle atomizer or metered-dose inhaler. Typical of atomizers are the Mistometer (Wintrop) and the Medihaler (Riker).

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The local delivery of the compositions of the invention can also be by a variety of techniques which administer the composition at or near the site of pain or anticipated pain. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

The formulations and compositions described herein may also contain other ingredients such as antimicrobial agents, or preservatives.

IV. Screening Assays

In yet another aspect, the present invention contemplates a process of screening substances for their ability to interact with a mutant μ opioid receptor polypeptide, the process comprising the steps of providing a polypeptide of the present invention, e.g., a recombinant cell transfected with a nucleic acid molecule of the invention, and testing the ability of selected substances to interact with that polypeptide.

Utilizing the methods and compositions of the present invention, screening assays for the testing of candidate substances such as agonists and antagonists of μ opioid receptors can be conducted. A candidate substance is a substance which can interact with or modulate, by binding or other intramolecular interaction, a μ opioid receptor polypeptide. In one embodiment, such a candidate substance is an antagonist of the wild-type receptor and an agonist of a mutant μ opioid receptor.

With the availability of cloned receptors, recombinant receptor screening systems have several advantages. A major advantage is that the investigator can control the type of receptor that is utilized in a screening assay. Specific receptor sub-types and sub-sub-types can be preferentially expressed and its interaction with a ligand can be identified. Other advantages include the availability of large amounts of receptor, and the availability of rare receptors previously unavailable in tissue samples.

Screening assays of the present invention generally involve determining the ability of a candidate substance to bind to the mutant receptor and to affect the activity of the receptor, such as the screening of candidate substances to identify those that inhibit or activate the receptor's function. Typically, this method includes preparing recombinant receptor polypeptide, followed by testing the recombinant polypeptide or cells expressing the polypeptide with a candidate substance to determine the ability of the substance to affect its physiological function. In preferred embodiments, the invention relates to the screening of candidate substances to identify those that are agonists of a mutant μ opioid receptor and an antagonist of the wild-type μ opioid receptor.

As is well-known in the art, a screening assay provides a receptor under conditions suitable for the binding of an agent to the receptor. These conditions include but are not limited to pH, temperature, tonicity, the presence of relevant co-factors, and relevant modifications to the polypeptide such as glycosylation or prenylation. It is contemplated that the receptor can be expressed and utilized in a prokaryotic or eukaryotic cell. The host cell expressing the receptor can be used whole or the receptor can be isolated from the host cell. The receptor can be membrane bound in the membrane of the host cell or it can be free in the cytosol of the host cell. The host cell can also be fractionated into sub-cellular fractions where the receptor can be found. For example, cells expressing the receptor can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/L and, more preferably from about 200 milliosmols per liter to about 400 mosm/L and, even more preferably from about 290 mosm/L to about 310 mosm/L. The presence of co-factors may be required for the proper functioning of the receptor. Typical co-factors include sodium, potassium, calcium, magnesium, and chloride. In addition, small, non-peptide molecules, known as prosthetic groups can be required. Other biological conditions needed for receptor function are well-known in the art.

It is well-known in the art that proteins can be reconstituted in artificial membranes, vesicles or liposomes (Danboldt et al., 1990). The present invention contemplates that the receptor can be incorporated into artificial membranes, vesicles or liposomes. The reconstituted receptor can be utilized in screening assays.

It is further contemplated that the receptor of the present invention can be coupled to a solid support. The solid support can be agarose beads, polyacrylamide beads, polyacrylic beads or other solid matrices capable of being coupled to proteins. Well-known coupling agents include cyanogen bromide, carbonyldiimidazole, tosyl chloride, and glutaraldehyde.

It is further contemplated that secondary polypeptides which can function in conjunction with the receptor of the present invention can be provided. For example, the receptor of the present invention exerts its physiological effects in conjunction with a G-protein and an effector polypeptide.

In a typical screening assay for identifying candidate substances, one employs the same recombinant expression host as the starting source for obtaining the receptor polypeptide, generally prepared in the form of a crude homogenate. Recombinant cells expressing the receptor are washed and homogenized to prepare a crude polypeptide homogenate in a desirable buffer such as disclosed herein. In a typical assay, an amount of polypeptide from the cell homogenate, is placed into a small volume of an appropriate assay buffer at an appropriate pH. Candidate substances, such as agonists and antagonists, are added to the admixture in convenient concentrations and the interaction between the candidate substance and the receptor polypeptide is monitored.

Where one uses an appropriate known substrate for the receptor, one can, in the foregoing manner, obtain a baseline activity for the recombinantly produced receptor. Then, to test for inhibitors or modifiers of the receptor function, one can incorporate into the admixture a candidate substance whose effect on the receptor is unknown. By comparing reactions which are carried out in the presence or absence of the candidate substance, one can then obtain information regarding the effect of the candidate substance on the normal function of the receptor.

Accordingly, it is proposed that this aspect of the present invention provides those of skill in the art with methodology that allows for the identification of candidate substances having the ability to modify the action of opioid receptor polypeptides in one or more manners.

In one embodiment, such an assay is designed to be capable of discriminating those candidate substances with the desirable properties of opioids but which lack the undesirable properties of opioids. In another embodiment, screening assays for testing candidate substances such as agonists and antagonists of mutant μ opioid receptors are used to identify such candidate substances having selective ability to interact with one or more of the opioid receptor polypeptides but which polypeptides are without a substantially overlapping activity with other opioid receptors.

In certain embodiments, the polypeptides of the invention are crystallized in order to carry out x-ray crystallographic studies as a means of evaluating interactions with candidate substances or other molecules with the opioid receptor polypeptide. For instance, the purified recombinant polypeptides of the invention, when crystallized in a suitable form, are amenable to detection of intra-molecular interactions by x-ray crystallography. An important aspect of the invention is the use of recombinantly produced mutant μ opioid receptor polypeptide in screening assays for the identification of substances which can activate the mutant receptor and inhibit the wild-type receptor.

The receptor can be expressed in a prokaryotic or a eukaryotic cell. A cell expressing a receptor can be used. For example, cells expressing the receptor of the present invention can be exposed to radiolabeled agent and the amount of binding of the radiolabeled agent to the cell can be determined. Alternatively, the cell expressing the receptor can be fractionated into sub-cellular components which contain the receptor of the present invention. Methods for purifying sub-cellular fractions are well-known in the art. Sub-cellular fractions include but are not limited to the cytoplasm, cellular membrane, other membranous fractions such as the endoplasmic reticulum, golgi bodies, vesicles and the nucleus. Receptors isolated as sub-cellular fractions can be associated with cellular membranes. For example, if cellular membrane vesicles are isolated from the cell expressing the receptor, the receptor molecule can be membrane bound. It is further contemplated that the receptor of the present invention can be purified from a cell that expresses the receptor. Methods of purification are well-known in the art. The purified receptor can be used in screening assays.

The detection of an interaction between an agent and a receptor can be accomplished through techniques well-known in the art. These techniques include but are not limited to centrifugation, chromatography, electrophoresis and spectroscopy. The use of isotopically labeled reagents in conjunction with these techniques or alone is also contemplated. Commonly used radioactive isotopes include $^3$H, $^{14}$C, $^{22}$Na, $^{32}$P, $^{35}$S, $^{45}$Ca, $^{60}$Co, $^{125}$I, and $^{131}$I. Commonly used stable isotopes include $^2$H, $^{13}$C, $^{15}$N, 18O.

For example, if an agent can bind to the receptor of the present invention, the binding can be detected by using radiolabeled agent or radiolabeled receptor. Briefly, if radiolabeled agent or radiolabeled receptor is utilized, the agent-receptor complex can be detected by liquid scintillation or by exposure to X-ray film.

Where a secondary polypeptide is provided, the agent-receptor-secondary polypeptide complex or the receptor-secondary polypeptide complex can be detected. Differences in mobility or differences in spectroscopic properties can be detected. It is further contemplated that where a secondary polypeptide is provided the enzymatic activity of the effector polypeptide can be detected. For example, many receptors exert physiological effects through the stimulation or inhibition of adenylyl cyclase. The enzymatic activity of adenylyl cyclase in the presence of an agent can be detected.

In preferred assays, an admixture containing the polypeptide, effector and candidate substance is allowed to incubate for a selected amount of time, and the resultant incubated mixture subjected to a separation means to separate the unbound effector remaining in the admixture from any effector/receptor complex so produced. Then, one simply measures the amount of each (e.g., versus a control to which no candidate substance has been added). This measurement can be made at various time points where velocity data is desired. From this, one can determine the ability of the candidate substance to alter or modify the function of the receptor.

Numerous techniques are known for separating the effector from effector/receptor complex, e.g., thin layer chromatographic methods (TLC), HPLC, spectrophotometric, gas chromatographic/mass spectrophotometric or NMR analyses. It is contemplated that any such technique can be employed so long as it is capable of differentiating between the effector and complex, and can be used to determine enzymatic function such as by identifying or quantifying the substrate and product. The effector/receptor complex itself can also be the subject of techniques such as x-ray crystallography. Where a candidate substance replaces the opioid molecule as the drug's mode of action, studies designed to monitor the replacement and its effect on the receptor will be of particular benefit.

The invention will be further described by the following non-limiting examples.

EXAMPLE I

Methods

Generation of Knock-In Mice

Figure 1:
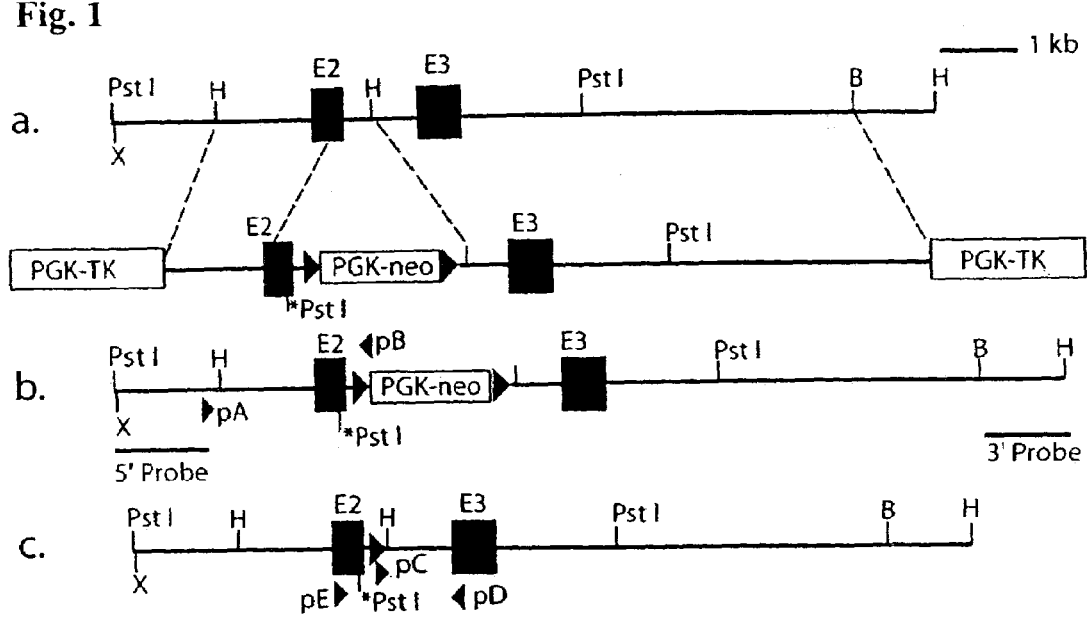
FIG. 1. Replacement of μ opioid receptor gene with a mutant gene encoding $\mu^{S196A}$. A) Schematic of a portion of the endogenous μ gene in a targeting vector. E2=exon 2; E3=exon 3; H=HindIII; B=BamHI; X=XhoI; PGK=phosphoglycerol kinase promoter; TK=thymidine kinase coding region; neo=coding region for neomycin resistance; and ▶=lox sites. B) Schematic of mutant μ opioid receptor allele in μ intron 2. PstI*=site of mutation after the first round of homologous recombination in ES cells and in mutant mice. C) Schematic of the mutant allele after breeding of the homozygous mutant mice with EIIa-cre transgenic mice showing the deletion of neo cassette.

Mouse μ opioid receptor genomic clones were obtained from a 129/ola mouse genomic DNA library by library screening using a mouse μ opioid receptor cDNA as the probe. Clone D3 containing exon 2 and flanking introns was used as the template to mutate the serine 196 codon of the μ opioid receptor to an alanine codon with two primers:
5'-AACTGGATCCTCTCTGCAGCCATTGGTCTG-3' (SEQ ID NO:1) and 5'-CAGACCAATGGCTGCAGAGAGGATCCAGTT-3' (SEQ ID NO:2). For selection purposes, a de novo PstI restriction site was created at the mutation site (FIG. 1). The mutated D3 clone was digested with EcoNI, a site 22 base pairs downstream from the splicing donor for intron 2, and the ends of the fragment were blunted by standard methodology. A LoxP-PGK-neo-LoxP fragment was obtained by restriction endonuclease digestion of vector P1338 (a gift from the ES core facility, Washington University, St. Louis), the ends blunted, and the blunt end fragment ligated to the intron 2 EcoNI site of the µ opioid receptor gene. The resulting clone was released from the vector by HindIII digestion and ligated to another µ opioid receptor gene fragment containing exon 3 and 3' flanking introns. The PGK-TK cassette was inserted on the ends of both arms of the homologous sequences as negative selection markers. SPI embryonic stem cells (a kind gift from the University of Texas, Austin) were transfected with the targeting construct, which was linearized with NotI and gel purified. After transfection, cells were selected by adding 300 µg/ml G418 and later 2 µM gancyclovir. Cells that underwent homologous recombination were verified by PCR with primers pA (5' CTCAATAAAGACCTCACACATAAAGCAG 3'; SEQ ID NO:3) and pB (5' GTATAGCATACATTATACGAAGT-TGTTGAAGCCG 3'; SEQ ID NO:4) and Southern blotting with both the 5' probe and the 3' probe (see FIG. 1B).

Two independent clones, clones #30 and #82, were used for the generation of knock-in mutant mice. Homozygous mutant mice were bred with EIIa-cre transgenic mice that express cre-recombinase in their early embryonal stages (Lakso et al., 1996). The expression of cre results in the deletion of the neo cassette in intron 2 of the µ opioid receptor gene. The deletion of the neo cassette was detected by PCR and later confirmed by Southern blotting using a neo fragment as a probe. After breeding with EIIa-cre transgenic mice, the F1 heterozygous mutant mice were bred to generate homozygous mutant mice, heterozygous mutant mice and wild-type littermates. The genotype of the mice was determined by digesting mouse genomic DNA with PstI and Southern blotting with the 5' probe.

Scatchard Analysis

Brain membranes were prepared from both wild-type mice and homozygous cre/S196A mice and heterozygous Cre/S196A mice. Approximately 200–350 µg of membranes were used in each assay. Saturation binding analysis was performed with varying concentrations of [$^3$H]DAMGO (0.001–12 nM) in the presence (nonspecific binding) or absence of 10 µM naloxone (Loh et al., 1998). Receptor density ($B_{max}$) and affinity ($K_d$) values for [$^3$H]DAMGO were calculated using non-linear one-site binding analysis of Graphpad-Prism and Scatchard plots.

Antinociception Testing

For tail withdrawal testing, mice were loosely wrapped in an adsorbent towel, and their tails were immersed about 2 cm into water heated to 53° C. or placed under radiant heat. The latency to tail withdrawal was recorded. A cut-off time of 24 seconds for warm water or 12 seconds for radiant heat was used to minimize tail damage. Tail withdrawal responses were recorded 30 minutes after morphine and nalorphine injection and 12 minutes after naloxone injection. Percent maximum possible effects (% MPE) were calculated by the following formula: (measured latency–baseline latency)*100/(cut-off time–baseline latency). Each dose for each genotype involved 8–12 mice. $ED_{50}$ values were derived from regression analysis on the linear portion of each dose-response curve or calculated by non-linear regression. A two way analysis of variance (ANOVA) (genotype and dose) was used to determine genetic differences among genotypes in the same dose groups.

Writhing tests were conducted as follows. Mice were injected with different doses of opioid drugs, and 20 minutes after the injection (5 minutes for naloxone), they were injected with 10 ml/kg 0.6% acetic acid (w/v) intraperitoneally (i.p.). Writhing was counted for 20 minutes following the i.p. injection. At the same time, mice from each genotype were injected with saline s.c. plus acetic acid i.p., and the mean count of writhing of the saline group was calculated. The % MPE for writhing test was calculated by the following formula: (mean count of saline group–count of drug group)*100/(mean count of saline group).

Results

Generation of Mutant Mice Expressing MOR$^{S196A}$

Previously it was reported that a mutation of Ser$^{196}$ of the µ opioid receptor to Leu resulted in naloxone exhibiting partial agonistic properties at this mutant receptor in vitro (Claude et al., 1996). In vitro experiments in which the Ser$^{196}$ residue was substituted with other amino acids indicated that a mutation of Ser$^{196}$ to Ala resulted in greater agonistic efficacy in classical opioid antagonists (Claude, 1997). To determine whether mutant µ opioid receptors have desirable properties in vivo, a targeting vector was designed that would replace the Ser$^{196}$ codon within the MOR-1 gene with that of Ala (FIG. 1). The homologous recombination events were screened in ES cells and in knock-in mice by PCR using primers pA and pB followed by Southern analysis using a $^{32}$P-labeled 5'-probe (FIG. 1). The ES cells and the homozygous mice were identified by a single PstI restricted fragment of about 2.5 kB (FIG. 2A). When the expression of the µ opioid receptor S196A mutant was evaluated in the homozygous mice that contained the neo cassette in intron 2, no detectable [$^3$H]DAMGO ([D-Ala$^1$.N-McPhe$^4$.Gly$^5$-ol]enkephalin) binding was observed. The absence of the receptor protein in these mice paralleled the low level of correctly spliced mRNA. When the primer pair pE (5' CTACATTTTCAACCTTGCTCTG 3'; SEQ ID NO:5) and pD (5' GAGCAGGTTCTCCCAGTACC 3'; SEQ ID NO:6) was used in the RT-PCR reaction, the amount of correctly spliced mRNA in the homozygous mice with the neo cassette in intron 2 was only 3% of that of the wild-type mice (FIGS. 2B and 2D). The presence of the incorrectly spliced mRNA in these mice could be demonstrated with the primer pair pE and pB (FIGS. 2C and 2D). At the same time, there was no detectable incorrectly spliced mRNA in the wild-type mice. These data suggested that the presence of the neo cassette within intron 2 of MOR-1 gene prevented the mRNA from being spliced correctly. The inclusion of intron 2 in the MOR-1 mRNA would introduce an early stop codon right after exon 2 and accounted for the undetectable level of functional receptors in these knock-in mice.

The homozygous knock-in mice were bred with EIIa-cre transgenic mice that constitutively express cre-recombinase in their early embryonic stages (Lakso et al., 1996). The deletion of the neo cassette from intron 2 was detected and confirmed by Southern analyses using a neo fragment as the probe (data not shown). When the MOR-1 mRNA in these mice was analyzed, it could be demonstrated that the deletion of neo cassette by cre-recombinase alleviated, although did not eliminate, the splicing problem. The PCR reaction using primer pair pE and pD revealed that the correctly spliced mRNA in these EIIa-cre transgenic mated knock-in mice (Cre/S196A mice) was about 48% of that of the wild-type mice (FIGS. 2B and 2D). Meanwhile, the incorrectly spliced MOR-1 mRNA in the Cre/S196A mice was only 10% of that in the knock-in mice with the neo cassette remaining in intron 2 (FIGS. 2C and 2D).

The presence of correctly spliced MOR-1 mRNA was also reflected in the [$^3$H]DAMGO binding, albeit at a drastically reduced level. When Scatchard analyses were carried out with the [$^3$H]DAMGO saturation binding studies using brain membranes prepared from wild-type and Cre/S196A mice, an about 85% decrease in the receptor expression level was observed in the homozygous mice ($B_{max}$=17.5±2.3 fmole/mg-protein in homozygous mice versus $B_{max}$=113±4.3 fmole/mg-protein in wild-type mice). There was no significant difference in the affinity of DAMGO for the wild-type and mutant receptors, with $K_d$ values equal to 2.6±0.3 nM and 6.3±3.6 nM respectively. This reduction in the μ opioid receptor level was due to the presence of a 42 bp loxP sequence in intron 2 after deletion of the neo cassette. Further analysis of the intron 2 sequence indicates that there are four AGGG repeats in the first 50 bp of the 5' region of intron 2. These repeats have been shown to play an important role in enhancing splicing of mRNA (Logan et al., 1997; Wendel et al., 1998). Thus, the presence of the 42 bp loxP sequence may have interfered with the function of these AGGG repeats and reduced the amount of correctly spliced MOR-1 mRNA in the Cre/S196A mice.

Figure 3A:
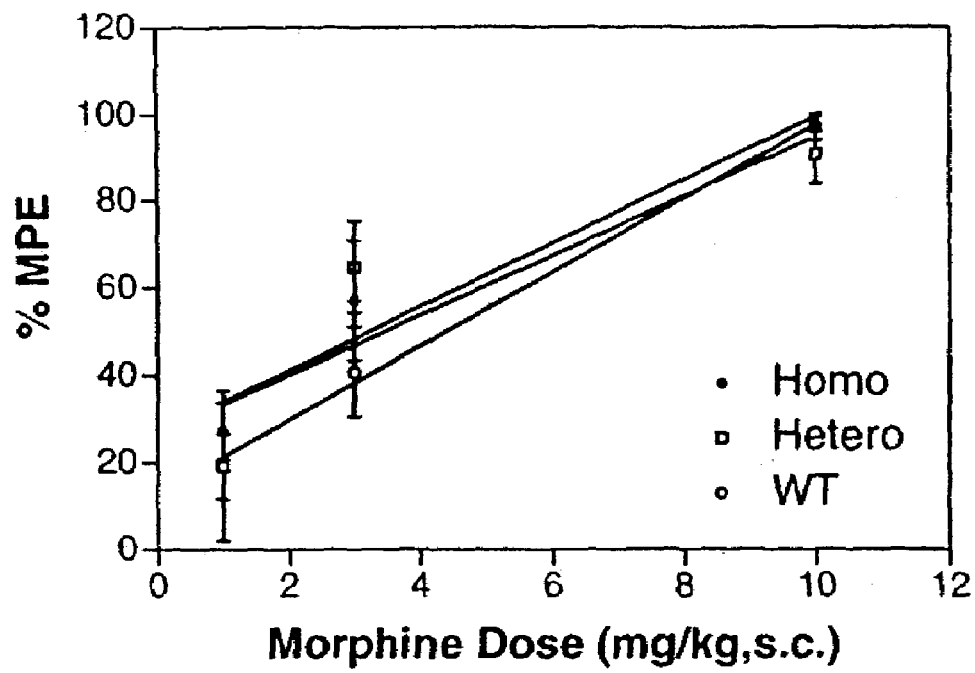
FIG. 3. Morphine antinociception in wild-type and Cre/S196A mice (A; tail withdrawal results; B; inhibition of writhing results). A) Homozygous (Homo) and heterozygous (Hetero) Cre/S196A mutant mice and their wild-type littermates (WT) were treated with various doses of morphine s.c. and the latencies of tail withdrawal from radiant heat recorded. $ED_{50}$ values were: 4.4 mg/kg (95% CI: 4.04–4.76 mg/kg) for wild-type, 3.2 mg/kg (95% CI 1.8–4.6 mg/kg) for homozygous, and 3.47 mg/kg (95% CI: 2.3–6.9 mg/kg) for heterozygous mice. Similar results were observed by using warm water (53° C.) as the heat source. B) $ED_{50}$ values were 0.48 mg/kg (95% CI: 0.30–1.30 mg/kg), 0.50 mg/kg (95% CI: 0.32–1.15 mg/kg), and 0.68 mg/kg (95% CI: 0.43–1.62 mg/kg) for wild-type, homozygous and heterozygous Cre/S196A mutant mice, respectively. Data are presented as the mean±s.e.m., n=8–12. There is no significant difference among genotypes for either test: P>0.05 by two-way ANOVA (genotype and dose).
Figure 3B:
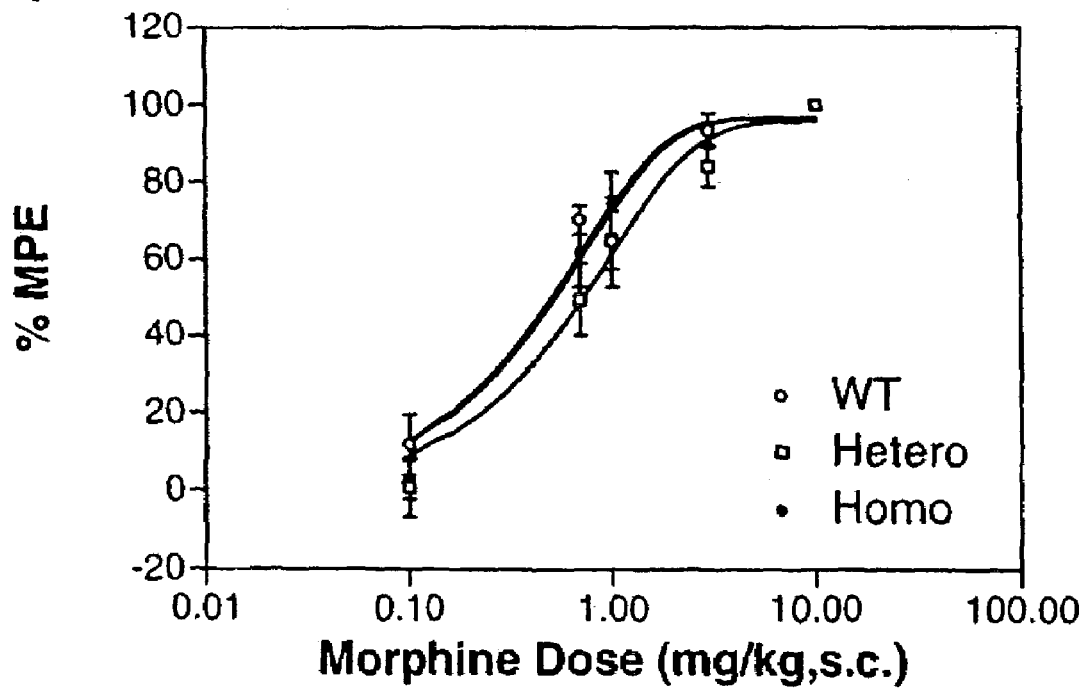

Morphine Retains Its Antinociception Effect with Comparable Potency and Efficacy The reduction in the amount of μ opioid receptors in Cre/S196A mice could have disrupted the in vivo activities of the opioid agonists. In μ opioid receptor knockout mice studies, several laboratories have reported that there are decreases in morphine antinociception potency in heterozygous mice (Loh et al., 1998; Sora et al., 1997). Hence, the antinociceptive properties of morphine in the MOR-1 knock-in mice was examined. Inhibition of tail withdrawal from either warm water (53° C.) or radiant heat, and inhibition of acetic acid-induced writhing, were used as the antinociceptive tests. Morphine, when injected subcutaneously, produced a dose-dependent inhibition of the tail withdrawal and the acetic acid-induced writhing in the wild-type animals. The $ED_{50}$ values for these two tests were determined to be 4.4 mg/kg (95% CI: 4.04–4.76 mg/kg) and 0.48 mg/kg (95% CI: 0.3–1.3 mg/kg). These values are within the norm of the reported morphine antinociceptive dosages for these two tests (Ho et al., 1976; Harris et al., 1975; Rubinstein et al., 1996). That morphine is more potent in inhibiting the writhing response is in accord with previously reported studies indicating that writhing inhibition is a more sensitive measurement of antinociception, which differs from tail withdrawal and hot plate antinociceptive tests in several ways (Mogil et al., 1996). Surprisingly, when these two tests were carried out with the heterozygous or homozygous knock-in mice, there was no statistical difference in the $ED_{50}$ values of morphine to produce antinociceptive effect in these mice as compared to the wild-type littermates (FIG. 3). Though there appeared to be a slight reduction in morphine potency in the heterozygous mice within the writhing test (FIG. 3B), the difference was not statistically significant from that of the wild-type mice. The observation that morphine was able to elicit the maximal antinociceptive response in mice with reduced receptor density was not surprising.

The ability of morphine to produce maximal antinoceptive responses in the heterozygous μ opioid receptor knockout mice and mice treated with certain doses of the μ opioid antagonists clocinnamox and beta-funaltrexaniine (13-FNA) have been reported (Lon et al., 1998; Walker et al., 1998; Zimmerman et al., 1987). However, in those animals, there was more than a two-fold reduction in the morphine potency. In MOR-1 knock-in mice, with about 36% reduction of receptor level in the heterozygous mice, or about a 85% reduction in the receptor content in homozygous mice (FIG. 2E), the potency of morphine to elicit the antinociceptive responses in these two tests was similar to that of the wild-type (FIG. 3). Since the binding studies with the brain membranes from these animals did not reveal any significant difference in the agonist affinity for the receptor (FIG. 2E), the similarity in the morphine potency among these mice suggested a probable increase in the coupling efficiency with the μ opioid receptor S196A mutant.

Naloxone Induces Antinociception in the Mutant Mice

Although the data indicated that the S196A mutation likely enhanced the coupling between the μ opioid receptor and the effector systems, necessitating lower receptor occupancy required for the full agonistic effects, agonist activation of these mutant receptors in vivo would not be distinguishable from the activation of the endogenous receptors. One probable in vivo difference between the S196A mutant and the wild-type receptor is the ability of classical antagonists to activate the mutant but not the wild-type receptor. In in vitro studies with the S196L mutation of the μ opioid receptor, Claude et al. (1996) reported the ability of naloxone or naltrexone to activate the G protein-coupled inwardly rectifying potassium channels (GIRK-1) and to inhibit the forskolin-stimulated adenylyl cyclase activity. The in vitro studies also indicated that these classical opioid antagonists possessed greater intrinsic efficacies in the S196A receptor mutant (Claude, 1997). Thus, naloxone may elicit antinociceptive responses in the Cre/S196A mice.

Figure 4A:
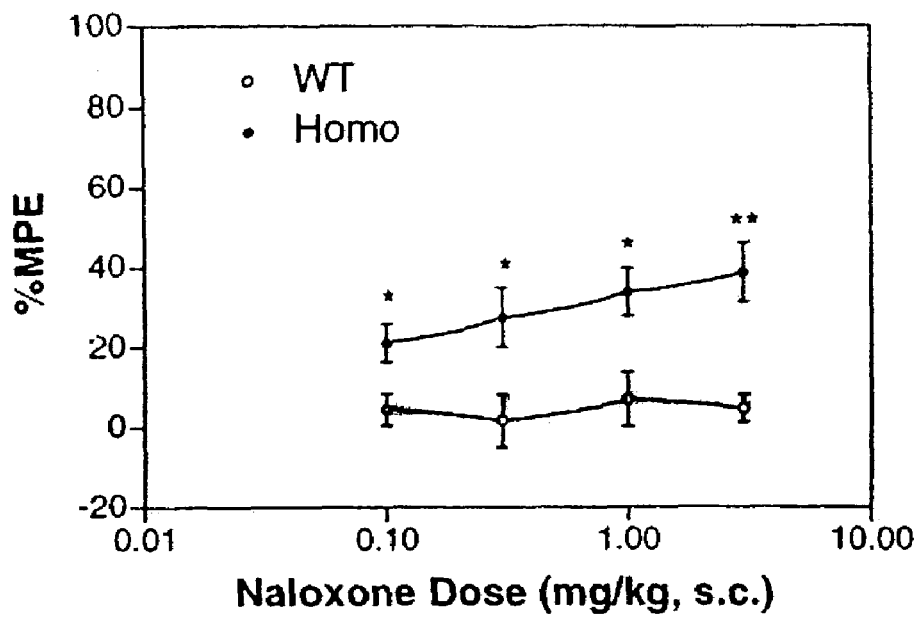
FIG. 4. Naloxone produces antinociceptive responses in Cre/S196A homozygous mice (A; tail withdrawal results; B; inhibition of writhing results). A) Homozygous Cre/S196A mice (Homo) and their wild-type littermates (WT) were injected with various doses of naloxone and the tail withdrawal latencies from radiant heat were recorded 12 minutes after naloxone injection. The $ED_{50}$ value for homozygous mice was 1.32 mg/kg (95% CI: 1.24–1.4 mg/kg). *: P<0.05, **: P<0.01, student's t-test between wild-type and homozygous mice in the same dose group, n=10–12. Similar results were observed using warm water (53° C.) as the heat source. B) Mice were injected with naloxone and 5 minutes later injected with 10 ml/kg 0.6% acetic acid (w/v) i.p. and writhing was assessed for the next 20 minutes. $ED_{50}$ value for the homozygous mice was 0.22 mg/kg (95% CI: 0.08–0.46 mg/kg). *: P<0.05, student's t-test between genotypes in the same dose groups.
Figure 4B:
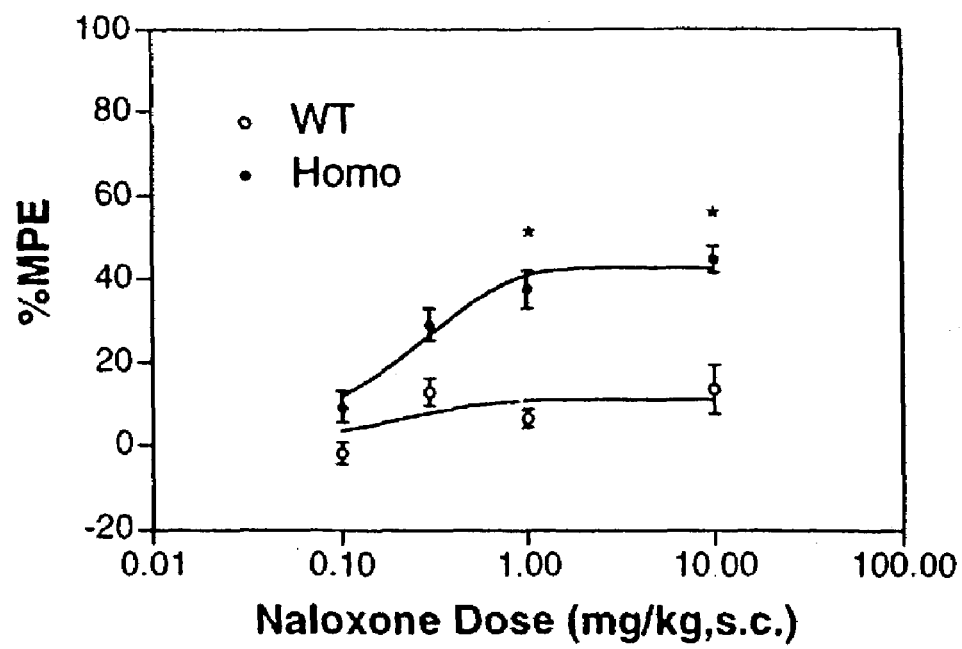

When naloxone, at doses of 0.1 to 10 mg/kg, was administered to wild-type mice, this opioid antagonist did not produce significant antinociceptive responses in either the tail withdrawal or writhing tests (FIG. 4). In contrast, when the same dosages of naloxone were administered to the Cre/S196A mice, there was an antagonist concentration-dependent antinociceptive responses. With the writhing inhibition test, the naloxone $ED_{50}$ value was determined to be 0.22 mg/kg (95% CI: 0.08–0.46 mg/kg). This potency compares favorably with the potency of morphine to inhibit the acetic acid-induced writhing responses, which is 0.5 mg/kg (95% CI: 0.3–1.1 mg/kg) (FIG. 3B). However, the maximal response was only 45±3 of that observed with morphine (FIG. 4B). Hence, in the writhing inhibition test, naloxone activated the S196A mutant receptor in the manner of a partial agonist. Similar observations were obtained with the tail withdrawal test. In all the doses tested, naloxone inhibited the tail withdrawal responses in the knock-in mice significantly as compared to the wild-type littermates (FIG. 4A). An accurate dose response curve was not obtained due to the increasing toxic effects of naloxone in both the mutant and the wild-type mice at higher dosages. Nevertheless, it is apparent that naloxone in the tail withdrawal test is less efficacious than morphine, as in the case of the writhing inhibition test. That naloxone behaves like a partial agonist in these in vivo tests is in accord with the in vitro observation that naloxone could only partially activate the GIRK-1 channels via the μ opioid receptor S196A mutant when compared to the agonist activation (Claude, 1997).

Nalorphine is More Efficacious in the Mutant Mice

If the S196A mutation increases the intrinsic efficacy of an opioid antagonist, it follows that the intrinsic efficacy of the partial agonists would be increased in these knock-in mutant mice as well. Nalorphine, a partial agonist on the μ opioid receptor with low efficacy (Zimmerman et al., 1987), was chosen to test this hypothesis. In agreement with previous reports, nalorphine inhibited the tail withdrawal and acetic acid-induced writhing responses in the wild-type mice (FIG. 5). The $ED_{50}$ values for nalorphine in inhibiting the tail withdrawal and writhing responses were 0.61 mg/kg (95% CI: 0.32–0.8 mg/kg) and 0.37 mg/kg (95% CI: 0.24–0.74 mg/kg), and the maximal nalorphine responses were 24±5% and 44±3% of the maximal morphine responses in the wild-type mice.

Figure 5A:
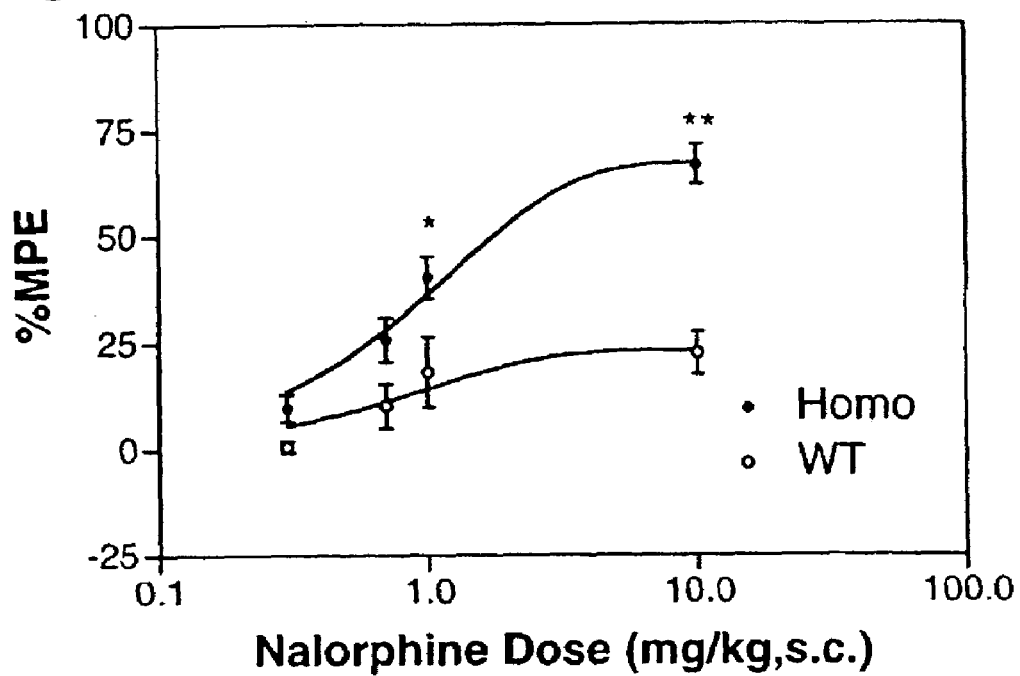
FIG. 5. Antinociceptive responses of nalorphine (A; tail withdrawal results; B; inhibition of writhing results). A) $ED_{50}$ values for homozygous Cre/S196A mice (Homo) and wild-type mice (WT) were 0.89 mg/kg (95% CI: 0.54–2.60 mg/kg) and 0.61 mg/kg (95% CI: 0.32–0.8 mg/kg) respectively. *: P<0.05; **: P<0.01, student's t-test as compared between genotypes in the same dose groups, n=8–10. B) $ED_{50}$ values were 0.27 mg/kg (95% CI: 0.13–0.61 mg/kg) for homozygous Cre/S196A mice and 0.37 mg/kg (95% CI.
Figure 5B:
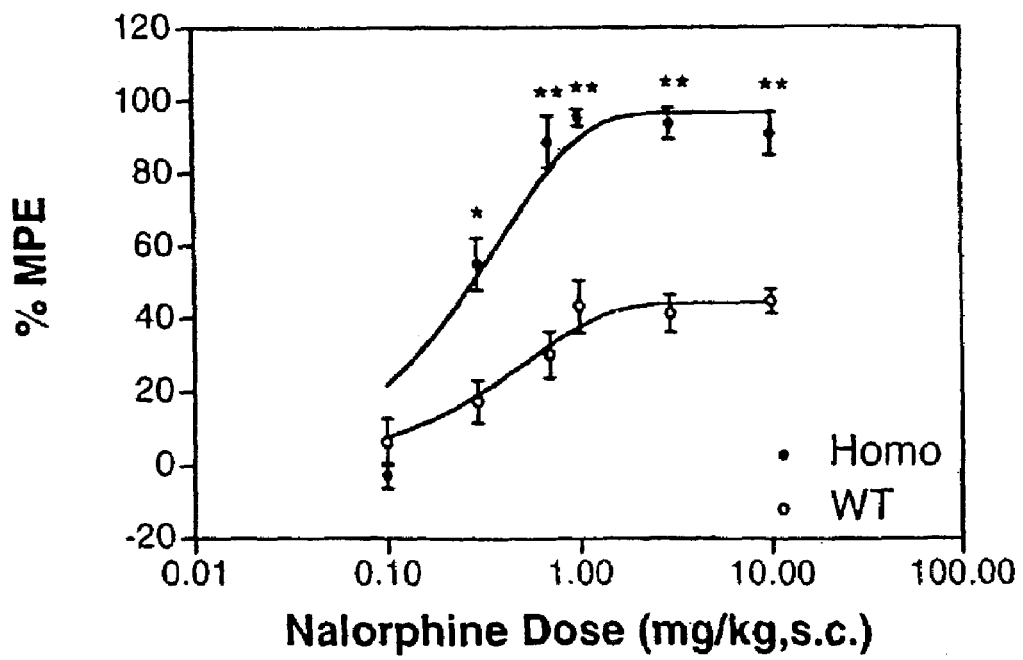

When the ability of nalorphine to induce antinociceptive responses in these two tests was measured in homozygous Cre/S196A mice, a significant increase in the maximal responses without alteration of the nalorphine's potency was observed (FIG. 5). In the tail withdrawal test, the nalorphine's potency in the mutant mice was determined to be 0.89 mg/kg (95% CI: 0.54–2.60 mg/kg). At the maximal dose tested, 10 mg/kg, nalorphine's antinociceptive response was 68±5% of the morphine maximal response (FIG. 5A). In contrast, in the inhibition of writhing test, at a dose of 1 mg/kg, nalorphine exhibited the same maximal antinociceptive response as morphine (FIG. 5B). The potency of nalorphine was determined to be 0.27 mg/kg (95% CI: 0.13–0.61 mg/kg). Thus, in the inhibition of writhing test, nalorphine behaved like a full agonist in the mutant receptor knock-in mice.

The difference in the nalorphine responses within the mutant mice in these two tests may be caused by differences in the receptors involved. Both μ and κ opioid receptors have been implicated in the inhibition of abdominal writhing in animals (Tyers, 1980; Friese et al., 1997). A decrease in the acetic acid threshold was observed in κ opioid receptor knockout animals (Simonin et al., 1998). Nalorphine has been proposed to be a κ opioid agonist based on behavioral observations in a chronic spinal disorder dog model and its activity against heat versus non-heat noxia (Tyers, 1980). Hence, it is possible that the observed increase in the nalorphine intrinsic efficacy was due to the activation of the κ opioid receptor or an undemonstrated μ/κ heterodimer in the mutant mice, as suggested by in vitro heterodimerization studies (Jordan et al., 1999). Since the opioid antagonists exhibit agonistic properties in the S196A receptor mutant, it is difficult to use receptor selective antagonists to delineate the specific opioid receptors involved in nalorphine response. Studies with μ opioid receptor selective antagonist β-FNA (Zimmerman et al., 1987), and the absence of nalorphine effect in μ opioid receptor knockout mice (data not shown), suggests that nalorphine antinoceptive responses are mediated via the μ opioid receptor. Therefore, it is likely that the increase in the nalorphine intrinsic efficacy in the mutant mice is due to the presence of the S196A mutation in the μ opioid receptor in these animals.

Discussion

The ability of the S196A mutation of the μ opioid receptor to increase the intrinsic efficacy of the opioid ligands was clearly demonstrated. Both the in vitro and in vivo naloxone responses indicated that this classical opioid antagonist possessed agonistic properties in the μ opioid receptor S196A mutant. Although the intrinsic efficacy of naloxone was observed to be that of a partial agonist, the ability of an antagonist to exhibit an antinociceptive effect in the mutant mice represents an unique opportunity to design paradigms for chronic pain treatment. In vitro data with the μ and δ opioid receptor chimeras suggested that interaction between transmembrane domains determines the efficacy of the opioid drugs (Claude, 1997). Improvement of naloxone intrinsic efficacy can be accomplished by mutating the interacting sites between certain transmembrane regions. For example, mutant μ opioid receptors with an amino acid substitution in TM4, e.g., S196A or S196L and an amino acid substitution in TM7, e.g., T327A or C330S, were activated by naloxone (FIG. 7). Currently, strong narcotic analgesic is given systemically or intrathecally to patients. Adjuvants or drug combinations are administered to alleviate the side effects of the analgesics (MacPherson, 2000). The present study shows that engineering receptor molecules can eliminate the side effects of opioid drugs while retaining their analgesic potency. For example, the loss of response during chronic administration of the drug (tolerance) could be prevented by the modification of the receptor domains that are involved in the chronic responses. Many studies have indicated that agonist-induced phosphorylation is one of the probable mechanisms for opioid receptor desensitization (Deng et al., 2000; Deng et al., 2001). Further, morphine tolerance was impeded in β-arrestin knockout mice (Bohn et al., 2000). Hence, by mutating the phosphorylation sites of the μ opioid receptor (e.g., Thr370 and Ser375 are phosphorylated in the presence of agonist in human cell lines), one or more residues in one or more transmembrane regions, or a combination thereof, its mutant receptors are generated in which naloxone produces an acute antinociceptive responses without inducing tolerance.

Thus, by engineering a delivery vehicle that contains cis-acting elements that control cell-specific expression, e.g., cis-acting elements of the μ opioid receptor gene (Choe et al., 1998; Ko et al., 1998), mutant receptors can be expressed in specific nociceptive neurons of a patient, which can be activated by an antagonist such as naloxone or naltrexone, while the endogenous opioid receptors remain inactive. By targeting specific regions that are involved in pain transmission, such as the substantia gelatinosa of the spinal cord, systemic administration of an antagonist of the μ opioid receptor results in the activation of the mutant receptors at those sites, while the endogenous receptor system remains inactive. Hence, pain relief can be accomplished without eliciting the side effects of narcotic drugs.

REFERENCES

Abdallah et al., *Biol. Cell*, 85: 1 (1995).
Adelman et al., *DNA*, 2: 183 (1983).
Bavaay and Merrifield, "The Peptides," eds. E. Gross and F. Meienhofer, Vol. 2 (Academic Press, 1980) pp. 3–285.
Bloomer et al., *J. Virol.*, 71:6641 (1997).
Bohn et al., *Nature,* 408:720 (2000).
Bruera, E. & Neumann, C. M. In Pain and updated review. Refresher course Seattle, Wash., 1999.
Carlezon et al., *Science*, 277:812 (1997).
Chang et al., *Nature,* 375:61 (1978).
Choe et al., *J. Biol. Chem.,* 273: 34926 (1998).
Clark-Lewis et al., *Meth. Enzymol.,* 287: 233 (1997).
Claude et al., *Proc. Natl. Acad. Sci. USA,* 93:5715 (1996).
Claude, Ph.D. Thesis, University of Minnesota (1997).
Cogan et al., *Hum. Mol. Genet.,* 6:909 (1997).
Crea et al., *Proc. Natl. Acad. Sci. U.S.A.,* 75: 5765 (1978).
Danboldt et al., *Biochem.,* 29:6734 (1990).
Deng et al., *Biochemistry,* 39:5492 (2000).
Deng et al., *Brain Res.,* 898:204 (2001).
Donnelly et al., *Ann. N.Y. Acad. Sci.,* 772: 40 (1995).
Erlich, ed., *PCR Technology*, (Stockton Press, NY, 1989).
Ferruti, et al., *Cris. Rev. Ther. Drug Carrier Sys.,* 2:117 (1986).
Friese et al., *Life Sci.,* 60:625 (1997).
Gabizon, et al., *Cancer Res.,* 50:6371 (1990).
Gilbert et al., *J. Pharmacol. Exp. Ther.,* 198:66 (1976).
Goeddel et al., *Nature,* 781:544 (1979).
Goeddel et al., *WAR,* 8:405 (1980).
Goeddel et al., *Nucleic Acids Res.,* 8: 4057 (1980).
Harris et al., *J. Pharmacol. Exp. Ther.,* 195:488 (1975).
Hess et al., *S. Adv. Enz. Reg.,* 7:149(1968).

Hitzeman et al., *JBC*, 255:2073 (1980).
Ho et al., *Life Sci.*, 18:1111 (1976).
Holland et al., *Biochem.*, 17:4900 (1978).
Itakura et al., *Nature*, 198:1056 (1977).
Jordan et al., *Nature*, 399:697 (1999).
Kaspar et al., *Proc. Natl. Acad. Sci. USA*, 99:2320 (2002).
Ko et al., *J. Biol. Chem.*, 273:27678 (1998).
Kong et al., *Biol. Chem.*, 268:23055 (1993).
Lakso et al., *Proc. Natl. Acad. Sci. USA*, 93:5860 (1996).
Lawn et al., *Nucleic Acids Res.*, 9: 6103 (1981).
Loh et al., *Brain Res. Mol. Brain Res.*, 54:321 (1998).
MacPherson, *Pharmacol. Ther.*, 88:163 (2000).
Meienhofer in "Hormonal Proteins and Peptides," ed.; C. H. Li, Vol. 2 (Academic Press, 1973), pp.48–267.
Merrifield, *J. Am. Chem. Soc.*, 85:2149 (1963).
Mogil et al., *Proc. Natl. Acad. Sci. USA*, 93:3048 (1996).
Molling, *J. Mol. Med.*, 75: 242 (1997).
Mullis et al., *Cold Spring Harbor Symp. Quant. Biol.*, 51: 263 (1987).
Naldini et al., *Proc. Natl. Acad. Sci. USA*, 193:11382 (1996).
Needleman and Wunsch, *J. Mol. Biol.* 48: 443 (1970).
Pardoll et al., *Immunity*, 3: 165 (1995).
Pearson and Lipman, *Proc. Natl. Acad. Sci. (U.S.A.)* 85: 2444 (1988).
Ranade, *J. Clin. Pharmacol.*, 29:685 (1989).
Rubinstein et al., *Proc. Natl. Acad. Sci. USA*, 93:3995 (1996).
Sambrook et al., *Molecular Cloning: A Laboratory Manual*, Cold Spring Harbor Laboratory Press, 3$^{rd}$ ed. (2001).
Siebwenlist et al., *Cell*, 20:264 (1980).
Simmons et al., *Science*, 276: 276 (1997)
Simonin et al., *Embo J.*, 17:886 (1998).
Smith and Waterman, *Adv. Appl. Math.* 2: 482 (1981).
Sora et al., *Proc. Natl. Acad. Sci. USA*, 94:1544 (1997).
Stevenson et al., *Immunol. Rev.*, 145: 211 (1995).
Stewart et al., *Solid Phase Peptide Synthesis*, W. H. Freeman Co., San Francisco (1969).
Tyers, *Br. J. Pharmacol.*, 69:503 (1980).
Viera et al., *Meth. Enzymol.*, 153: 3 (1987).
Walker et al., *Psychopharmacology (Berl)*, 136:15 (1998).
Wendel et al., *J. Mol. Med.*, 76:525 (1998).
Yang et al., *Mol. Med. Today*, 2, 476 (1996).
Zimmerman et al., *J. Pharmacol. Exp. Ther.*, 241:374 (1987).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. An isolated nucleic acid molecule comprising a nucleic acid sequence encoding a full-lenath mutant µ opioid receptor or an active fragment thereof two or more amino acid substitutions in one or more transmembrane regions of the receptor, wherein at least one substitution is in the fourth transmembrane region, wherein the mutant receptor has the property of being activated when contacted with an antagonist of a corresponding wild-type µ opioid receptor, and wherein the two or more amino acid substitutions are at a position corresponding to position 196, 327 or 330 in the murine µ opioid receptor having SEQ ID NO:8.

2. The nucleic acid molecule of claim 1 wherein the nucleic acid sequence encodes a mutant receptor with two amino acid substitutions.

3. The nucleic acid molecule of claim 1 wherein the amino acid substitution at position 196 results in a mutant opioid receptor with the property of one having a seine to leucine substitution at position 196.

4. The nucleic acid molecule of claim 1 wherein the amino acid substitution at position 196 is serine to alanine, phenylalanine, glycine or leucine.

5. The nucleic acid molecule of claim 1 wherein the amino acid substitution at position 327 results in a mutant opioid receptor with the property of one having a threonine to alanine substitution at position 327.

6. The nucleic acid molecule of claim 1 wherein the amino acid substitution at position 327 is threonine to alanine.

7. The nucleic acid molecule of claim 1 wherein the amino acid substitution at position 330 results in a mutant opioid receptor with the property of one having a cysteine to serine at position 330.

8. The nucleic acid molecule 1 wherein the amino acid substitution at position 330 is cysteine to serine.

9. An expression cassette comprising a promoter operably linked to the nucleic acid molecule of claim 1.

10. The expression cassette of claim 9 wherein the promoter is expressed in neurons.

11. The expression cassette of claim 9 wherein the promoter is the µ opioid receptor promoter.

12. A vector comprising the expression cassette of claim 9.

13. The vector of claim 12 which is a viral vector.

14. An isolated host cell augmented with the expression cassette of claim 9.

15. A method to identify an agent that is an agonist of a mutant µ opioid receptor and an antagonist of a wild-type µ opioid receptor, comprising:
   a) contacting one or more agents with i) a mutant µ opioid receptor encoded by the nucleic acid molecule of claim 1, and ii) a wild-type µ opioid receptor; and
   b) identifying an agent which is an agonist of the mutant µ opioid receptor and an antagonist of the wild-type µ opioid receptor.

16. A method to detect a mutant µ opioid receptor which is activated upon contact with an antagonist of a corresponding wild-type µ opioid receptor, comprising:

a) contacting an antagonist of a wild-type μ opioid receptor with a mutant μ opioid receptor encoded by the nucleic acid molecule of claim 1; and b) detecting or determining whether the antagonist is an agonist of the mutant μ opioid receptor.

17. The method of claim 15 or 16 wherein the nucleic acid molecule encodes a mutant receptor with two amino acid substitutions.

18. The method of claim 15 or 16 wherein the mutant receptor comprises one amino acid substitution in the fourth transmembrane region and one amino acid substitution in the seventh transmembrane region.

19. The method of claim 15 or 16 wherein the amino acid substitution at position 196 is serine to leucine, alanine, glycine or phenylalanine.

20. The method of claim 15 or 16 wherein the amino acid substitution at position 196 results in a mutant opioid receptor with the properties of one having a serine to leucine substitution at position 196.

21. The method of claim 15 or 16 wherein the amino acid substitution at position 327 results in a mutant opioid receptor with the property of one having a threonine to alanine substitution at position 327.

22. The method of claim 15 or 16 wherein the amino acid substitution at position 327 is threonine to alanine.

23. The method of claim 15 or 16 wherein the amino acid substitution at position 330 results in a mutant opioid receptor with the property of one having a cysteine to serine substitution at position 330.

24. The method of claim 15 or 16 wherein the amino acid substitution at position 330 is cysteine to serine.

* * * * *

UNITED STATES PATENT AND TRADEMARK OFFICE
CERTIFICATE OF CORRECTION

PATENT NO. : 7,214,534 B2
APPLICATION NO. : 10/465172
DATED : May 8, 2007
INVENTOR(S) : Law et al.

It is certified that error appears in the above-identified patent and that said Letters Patent is hereby corrected as shown below:

In column 1, line 67, delete "$\mu\delta 2$" and insert -- $\mu\delta_2$ --, therefor.

In column 3, line 16, delete "tissueor" and insert -- tissue- or --, therefor.

In column 5, line 31, delete "occuring" and insert -- occurring --, therefor.

In column 10, line 26, delete "oploid" and insert -- opioid --, therefor.

In column 13, line 52 (Approx.), delete "gin" and insert -- gln --, therefor.

In column 18, line 15, delete "marcesceus" and insert -- marcescens --, therefor.

In column 19, line 13, delete "utlization" and insert -- utilization --, therefor.

In column 20, line 16, delete "iniraarterial" and insert -- intraarterial --, therefor.

In column 20, line 28, before "which" delete "of the invention". (Second Occurrence)

In column 21, line 62, delete "formulatory" and insert -- formulary --, therefor.

In column 22, line 66, delete "gelatine" and insert -- gelatin --, therefor.

In column 23, lines 1-2, delete "which the powder may be administered with the aid of an inhalator, insufflator or a metered-dose inhaler." and insert the same on Col. 22, Line 67, after "from".

In column 23, line 6, delete "(Wintrop)" and insert -- (Winthrop) --, therefor.

In column 25, lines 34-38, after "crystallography" delete ". An important aspect of the invention is the use of recombinantly produced mutant $\mu$ opioid receptor polypeptide in screening assays for the identification of substances which can activate the mutant receptor and inhibit the wild-type receptor." and insert the same on Col. 25, Line 35 as a new Paragraph.

In column 25, line 67, delete "18O" and insert -- $^{18}O$ --, therefor.

In column 27, line 7, delete "SPI" and insert -- SP1 --, therefor.

In column 27, line 11, delete "gancyclovir" and insert -- ganciclovir --, therefor.

UNITED STATES PATENT AND TRADEMARK OFFICE
CERTIFICATE OF CORRECTION

PATENT NO. : 7,214,534 B2
APPLICATION NO. : 10/465172
DATED : May 8, 2007
INVENTOR(S) : Law et al.

It is certified that error appears in the above-identified patent and that said Letters Patent is hereby corrected as shown below:

In column 27, line 34, delete "cre/S196A" and insert -- Cre/S196A --, therefor.

In column 27, line 62, delete "Writhing" and insert -- Writing --, therefor.

In column 29, line 58, delete "funaltrexaniine" and insert -- funaltrexamine --, therefor.

In column 34, line 5, after "(1997)" insert -- . --.

In column 41, line 40 (Approx.), in Claim 1, delete "full-lenath" and insert -- full-length --, therefor.

In column 41, line 56 (Approx.), in Claim 3, delete "seine" and insert -- serine --, therefor.

In column 44, line 3, in Claim 20, delete "properties" and insert -- property --, therefor.

Signed and Sealed this

Sixteenth Day of October, 2007

JON W. DUDAS
*Director of the United States Patent and Trademark Office*